(12) United States Patent
Wasan et al.

(10) Patent No.: US 8,592,382 B2
(45) Date of Patent: Nov. 26, 2013

(54) FORMULATIONS FOR THE ORAL ADMINISTRATION OF THERAPEUTIC AGENTS AND RELATED METHODS

(75) Inventors: Kishor M. Wasan, Richmond, CA (US); Ellen K. Wasan, Richmond, CA (US)

(73) Assignee: The University of British Columbia, Vancouver (CA)

( * ) Notice: Subject to any disclaimer, the term of this patent is extended or adjusted under 35 U.S.C. 154(b) by 86 days.

(21) Appl. No.: 12/601,676

(22) PCT Filed: May 23, 2008

(86) PCT No.: PCT/CA2008/000975
§ 371 (c)(1),
(2), (4) Date: Jun. 30, 2010

(87) PCT Pub. No.: WO2008/144888
PCT Pub. Date: Dec. 4, 2008

(65) Prior Publication Data
US 2010/0273728 A1    Oct. 28, 2010

Related U.S. Application Data

(60) Provisional application No. 60/940,307, filed on May 25, 2007, provisional application No. 60/976,708, filed on Oct. 1, 2007, provisional application No. 61/041,478, filed on Apr. 1, 2008.

(51) Int. Cl.
*A61K 31/70* (2006.01)

(52) U.S. Cl.
USPC .......................................................... 514/31

(58) Field of Classification Search
USPC .......................................................... 514/31
See application file for complete search history.

(56) References Cited

U.S. PATENT DOCUMENTS

| | | | |
|---|---|---|---|
| 5,444,052 A | 8/1995 | Pieringer et al. | |
| 6,294,192 B1 | 9/2001 | Patel et al. | |
| 6,660,761 B2 | 12/2003 | Khanuja | |
| 6,770,290 B1 * | 8/2004 | Proffitt et al. | 424/450 |
| 6,852,334 B1 | 2/2005 | Cullis et al. | |
| 6,923,988 B2 | 8/2005 | Patel et al. | |
| 7,053,061 B2 * | 5/2006 | Pai et al. | 514/31 |
| 7,060,285 B2 | 6/2006 | Muller | |
| 7,326,691 B2 | 2/2008 | Duddu et al. | |
| 8,067,032 B2 | 11/2011 | Chaubal et al. | |
| 2004/0146538 A1 | 7/2004 | Benameur et al. | |
| 2005/0112188 A1 | 5/2005 | Eliaz et al. | |
| 2005/0191343 A1 | 9/2005 | Liang | |
| 2008/0286373 A1 | 11/2008 | Palepu et al. | |

FOREIGN PATENT DOCUMENTS

| | | | |
|---|---|---|---|
| CA | 2526616 A1 | 12/2004 | |
| CA | 2604943 A1 | 10/2006 | |
| CN | 1897918 A | 1/2007 | |
| EP | 1170003 A1 | 1/2002 | |
| EP | 1661557 A1 | 5/2006 | |
| EP | 1328254 B1 | 2/2007 | |
| JP | 2003252750 A | 9/2003 | |
| WO | 95/08983 A1 | 4/1995 | |
| WO | 03/093344 A1 | 11/2003 | |
| WO | 2004/034992 A2 | 4/2004 | |
| WO | 2004/050068 A1 | 6/2004 | |
| WO | 2005/048952 A | 6/2005 | |
| WO | WO2008058234 A2 | 5/2008 | |

OTHER PUBLICATIONS

International Search Report of PCT/CA2008/000975 mailed Sep. 29, 2008.
Written Opinion of PCT/CA2008/000975 mailed Sep. 29, 2008.
Risovic, V. et al. "Potential Mechanisms by Which Peceol Increases the Gastrointestinal Absorption of Amphotericin B", Drug Development and Industrial Pharmacy, vol. 30, No. 7, p. 767-774, 2004.
Cruz, F.S. et al. "Prevention of Transfusion-Induced Chagas' Disease by Amphotericin B", Am. J. Trop.. Hyg., 29(5), p. 761-765, 1980.
Amphotericin B (Amphotericin B): instructions for use, contraindications, and the price of (http://www.rlsnet.ru/tn__index__id__4172.htm).
Deleers, M. et al., "Facilitated fusion of liposomes with glycerol monoleate planar bilayer", FEBS Letters, Elsevier, Amsterdam, NL, vol, 132, No. 2, 1981, p. 224-226.
Shah, N.H. et al., "Self-emulsifying drug delivery systems (SEDDS) with polyglycolyzed glycerides for improving in vitro dissolution and oral absorption of lipophilic drugs", International Journal of Pharmaceutcs, Elsevier BV, NL, vol. 106, No. 1, 1994, p. 15-23.
Hauss, D.J., et al., "Lipid-Based Delivery Systems for Improving the Bioavailability and Lymphatic Transport of a Poorly Water-Soluble LTB4 Inhibitor," Journal of Pharmaceutical Sciences 87(2)164-169, Feb. 1998.
Notice of Reasons for Rejection mailed Feb. 18, 2013, issued in corresponding Japanese Application No. 2010-508677, filed May 23, 2008, 10 pages.
Bittner, B., et al., "Improvement of the Bioavailability of Colchicine in Rats by Co-Administration of D-α-Tocopherol Polyethylene Glycol 1000 Succinate and a Polyethoxylated Derivative of 12-Hydroxy-Stearic Acid," Arzneimittel-Forschung/Drug Research 52(9):684-688, Sep. 2002.
Collnot, E.-M., et al., "Mechanism of Inhibition of P-Glycoprotein Mediated Efflux by Vitamin E TPGS: Influence on ATPase Activity and Membrane Fluidity," Molecular Pharmaceutics 4(3):465-474, May-Jun. 2007.
Communication Pursuant to Article 94(3) EPC dated Jul. 17, 2013, issued in corresponding European Application No. 08748337.6, filed May 23, 2008, 7 pages.
Karatas, A., et al., "Improved Solubility and Dissolution Rate of Piroxicam Using Gelucire 44/14 and Labrasol," II Farmaco 60(9):777-782, Sep. 2005.
Soliman, M.S., and M.A. Khan, "Preparation and In Vitro Characterization of a Semi-Solid Dispersion of Flurbiprofen With Gelucire 44/14 and Labrasol," Die Pharmazie—An International Journal of Pharmaceutical Sciences 60(4):288-293, Apr. 2005.
Notification of the Third Office Action, dated Jul. 29, 2013, issued in corresponding Chinese Application No. 200880023444.X, filed May 23, 2008, 10 pages.

* cited by examiner

*Primary Examiner* — Elli Peselev
(74) *Attorney, Agent, or Firm* — Christensen O'Connor Johnson Kindness PLLC

(57) ABSTRACT

The present application relates to an oral formulation of amphotericin B and other therapeutic agents, which formulation comprises one or more fatty acid glycerol esters and one or more PEG modified phospholipids or fatty acid esters. The formulation provides enhanced bioavailability and/or increased stability of the therapeutic agent at the low pH found in gastric fluid.

17 Claims, 20 Drawing Sheets

US 8,592,382 B2

FORMULATIONS FOR THE ORAL ADMINISTRATION OF THERAPEUTIC AGENTS AND RELATED METHODS

CROSS-REFERENCES TO RELATED APPLICATIONS

This application is the National Stage of International Application No. PCT/CA2008/000975, filed May 23, 2008, which claims the benefit of U.S. Provisional Application No. 60/940,307, filed May 25, 2007, U.S. Provisional Application No. 60,976,703, filed Oct. 1, 2007, and U.S. Provisional Application No. 61/041,478, filed Apr. 1, 2008. Each application is expressly incorporated herein by reference in its entirety.

BACKGROUND OF THE INVENTION

Each year in the Indian subcontinent alone, over 500,000 individuals play host to *Leishmania donovani*, an insidious parasite that invades macrophages, rapidly infiltrates the vital organs and ultimately leads to severe infection of the visceral reticuloendothelial system. Visceral leishmaniasis, also known as Kala-azar, is most prevalent in the weak and the young within a population. Left untreated, almost all infected individuals will die. Visceral leishmaniasis affects over 200 million people from 62 countries. The therapeutic arsenal against *Leishmania* is limited to a small number of parenterally administered agents, with daily injections of pentavalent antimony compound. Although more expensive than the antimonials, amphotericin B (AmpB) has a 97% cure rate and no reported resistance. However, drug therapy involves IV administration over 30-40 days and is associated with infusion-related side-effects (fever, chills, bone pain, thrombophlebitis). The dose-limiting toxicity, which may even affect the ability to achieve a cure, is renal impairment. In addition, due to the prohibitive cost and difficult route of drug administration, amphotericin B is failing to reach many patients.

In developed nations, disseminated fungal infections such as candidiasis, histoplasmosis, coccidiosis, and aspergillosis are on the rise, affecting patients with cancer, organ transplant recipients, diabetics and those with HIV/AIDS. In these patients, invasive fungal infections may account for as many as 30% of deaths. Despite the development of a number of new antifungal agents, amphotericin B formulated as an IV administered micelle and liposomal dispersion remains one of the most effective agents in the treatment of systemic fungal infections. In addition, a variety of parenteral formulation approaches have been studied for AmpB. While effective, the limitations of these parenteral formulations of amphotericin B are the safety issues associated with administration (infection of the indwelling catheter, patient chills and shaking due to RBC haemolysis, dose-dependent renal toxicity), feasibility of administration of parenteral products in remote locations and high drug cost.

The development of an effective and safe oral formulation of amphotericin B that would have significant applications in the treatment of disseminated fungal infections and would dramatically expand access to treatment of visceral leishmaniasis. However, the bioavailability of AmpB is negligible due to low aqueous solubility and instability at the low pH found in gastric fluid. Such limitations also apply to a variety of other therapeutic agents for which oral formulations are desirable.

A need exists for effective and safe oral formulations of amphotericin B as well as many other therapeutic agents that provide for enhanced bioavailability and/or increased stability of the therapeutic agent of interest the low pH found in gastric fluid. The present invention seeks to fulfill these needs and provides further related advantages.

SUMMARY OF THE INVENTION

The present invention provides compositions for formulating therapeutic agents, therapeutic agent formulations based on the compositions, methods for administering therapeutic agents using the formulations, and methods for treating conditions and diseases using the formulations.

In one aspect, the invention provides an amphotericin B formulation, comprising,
 (a) amphotericin B;
 (b) one or more fatty acid glycerol esters; and
 (c) one or more polyethylene oxide-containing phospholipids or one or more polyethylene oxide-containing fatty acid esters.

In one embodiment, amphotericin B is present in the formulation in an amount from about 0.5 to about 10 mg/mL of the formulation. In one embodiment, amphotericin B is present in the formulation in about 5 mg/mL. In another embodiment, amphotericin B is present in the formulation in about 7 mg/mL.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing phospholipids comprise a C8-C22 saturated fatty acid ester of a phosphatidyl ethanolamine polyethylene glycol salt. In one embodiment, the polyethylene oxide-containing phospholipids comprise a distearoylphosphatidyl ethanolamine polyethylene glycol salt. In one embodiment, the distearoylphosphatidyl ethanolamine polyethylene glycol salt is selected from the group consisting of a distearoylphosphatidyl ethanolamine polyethylene glycol 350 salt, a distearoylphosphatidyl ethanolamine polyethylene glycol 550 salt, a distearoylphosphatidyl ethanolamine polyethylene glycol 750 salt, a distearoylphosphatidyl ethanolamine polyethylene glycol 1000 salt, a distearoylphosphatidyl ethanolamine polyethylene glycol 2000 salt, and mixtures thereof. In one embodiment, the distearoylphosphatidyl ethanolamine polyethylene glycol salt is present in the formulation in an amount from 1 mM to about 30 mM based on the volume of the formulation. In one embodiment, the distearoylphosphatidyl ethanolamine polyethylene glycol salt is an ammonium salt or a sodium salt.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters is selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 60:40 v/v.

In one embodiment, the formulation further comprises glycerol in an amount less than about 10% by weight.

In one embodiment, the formulation is a self-emulsifying drug delivery system.

In another aspect, the invention provides a method for administering amphotericin B, comprising administering an amphotericin B formulation of the invention to a subject in need thereof. In one embodiment, the formulation is administered orally. In another embodiment, the formulation is administered topically.

In another aspect, the invention provides a method for treating an infectious disease treatable by the administration of amphotericin B, comprising administering to a subject in need thereof a therapeutically effective amount of an amphotericin B formulation of the invention. In one embodiment, the formulation is administered orally. In another embodiment, the formulation is administered topically.

Diseases treatable by the formulations include fungal infections, visceral leishmaniasis, cutaneous leishmaniasis, Chagas disease, Alzheimer's disease, or Febrile neutropenia. Fungal infections treatable by the formulations include aspergillosis, blastomycosis, candidiasis, coccidioidomycosis, crytococcosis, histoplasmosis, mucormycosis, paracoccidioidomycosis, or sporotrichosis.

In another aspect, the invention provides a formulation for the delivery of a therapeutic agent, comprising, (a) a therapeutic agent;

(b) one or more fatty acid glycerol esters; and (c) one or more polyethylene oxide-containing phospholipids or one or more polyethylene oxide-containing fatty acid esters.

In one embodiment, the therapeutic agent is present in the formulation in an amount from about 0.1 mg/mL to about 25 mg/mL of the formulation.

In certain embodiments, the therapeutic agent is selected from the group consisting of anticancers, antibiotics, antiviral drugs, antimycotics, anti-prions, anti-amoebics, non-steroidal anti-inflammatory drugs, anti-allergics, immunosuppressive agents, coronary drugs, analgesics, local anesthetics, anxiolytics, sedatives, hypnotics, migraine relieving agents, drugs against motion sickness, and anti-emetics.

In certain embodiments, the therapeutic agent is selected from the group consisting of tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfiram, vitamin K, paclitaxel, docetaxel, camptothecin, SN38, cisplatin, and carboplatin.

In one embodiment, the formulation further comprises a second therapeutic agent.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing phospholipids comprise a C8-C22 saturated fatty acid ester of a phosphatidyl ethanolamine polyethylene glycol salt. In one embodiment, the polyethylene oxide-containing phospholipids comprise a distearoylphosphatidyl ethanolamine polyethylene glycol salt. In one embodiment, the distearoylphosphatidyl ethanolamine polyethylene glycol salt is selected from the group consisting of a distearoylphosphatidyl ethanolamine polyethylene glycol 350 salt, a distearoylphosphatidyl ethanolamine polyethylene glycol 550 salt, a distearoylphosphatidyl ethanolamine polyethylene glycol 750 salt, a distearoylphosphatidyl ethanolamine polyethylene glycol 1000 salt, a distearoylphosphatidyl ethanolamine polyethylene glycol 2000 salt, and mixtures thereof. In one embodiment, the distearoylphosphatidyl ethanolamine polyethylene glycol salt is present in the formulation in an amount from 1 mM to about 30 mM based on the volume of the formulation. In one embodiment, the distearoylphosphatidyl ethanolamine polyethylene glycol salt is an ammonium salt or a sodium salt.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters is selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 60:40 v/v.

In one embodiment, the formulation further comprises glycerol in an amount less than about 10% by weight.

In one embodiment, the formulation is a self-emulsifying drug delivery system.

In another aspect, the invention provides a method for administering a therapeutic agent, comprising administering a therapeutic agent formulation of the invention to a subject in need of such agent. In one embodiment, the formulation is administered orally. In another embodiment, the formulation is administered topically.

In another aspect, the invention provides a composition for formulating a therapeutic agent, comprising, (a) one or more fatty acid glycerol esters; and (b) one or more polyethylene oxide-containing phospholipids or one or more polyethylene oxide-containing fatty acid esters.

In one embodiment, the fatty acid glycerol esters comprise from about 32 to about 52% by weight fatty acid monoglycerides. In one embodiment, the fatty acid glycerol esters comprise from about 30 to about 50% by weight fatty acid diglycerides. In one embodiment, the fatty acid glycerol esters comprise from about 5 to about 20% by weight fatty acid triglycerides. In one embodiment, the fatty acid glycerol esters comprise greater than about 60% by weight oleic acid mono-, di-, and triglycerides.

In one embodiment, the polyethylene oxide-containing phospholipids comprise a C8-C22 saturated fatty acid ester of a phosphatidyl ethanolamine polyethylene glycol salt. In one embodiment, the polyethylene oxide-containing phospholipids comprise a distearoylphosphatidyl ethanolamine polyethylene glycol salt. In one embodiment, the distearoylphosphatidyl ethanolamine polyethylene glycol salt is selected from the group consisting of a distearoylphosphatidyl ethanolamine polyethylene glycol 350 salt, a distearoylphosphatidyl ethanolamine polyethylene glycol 550 salt, a distearoylphosphatidyl ethanolamine polyethylene glycol 750 salt, a distearoylphosphatidyl ethanolamine polyethylene glycol 1000 salt, a distearoylphosphatidyl ethanolamine polyethylene glycol 2000 salt, and mixtures thereof. In one embodiment, the distearoylphosphatidyl ethanolamine polyethylene glycol salt is present in the formulation in an amount from 1 mM to about 30 mM based on the volume of the formulation. In one embodiment, the distearoylphosphatidyl ethanolamine polyethylene glycol salt is an ammonium salt or a sodium salt.

In one embodiment, the polyethylene oxide-containing fatty acid esters comprise a polyethylene oxide ester of a C8-C22 saturated fatty acid. In one embodiment, the polyethylene oxide-containing fatty acid esters comprise a polyethylene oxide ester of a C12-C18 saturated fatty acid. In one embodiment, the polyethylene oxide-containing fatty acid esters is selected from the group consisting of lauric acid esters, palmitic acid esters, stearic acid esters, and mixtures thereof. In one embodiment, the polyethylene oxide-containing fatty acid esters comprise a polyethylene oxide having an average molecular weight of from about 750 to about 2000.

In one embodiment, the composition further comprises glycerol in an amount less than about 10% by weight.

In another aspect, the invention provides a method for formulating a therapeutic agent, comprising combining a therapeutic agent with a composition of the invention for formulating a therapeutic agent.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
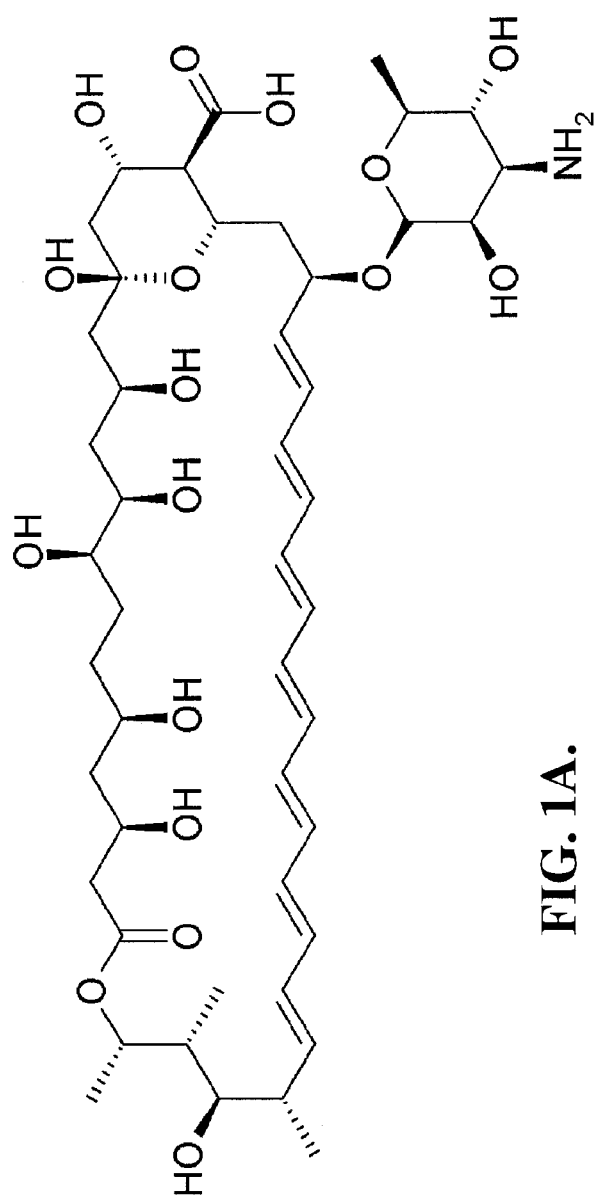
FIG. 1A illustrates the chemical structure of amphotericin B (AmpB).

The present invention provides compositions for formulating therapeutic agents. The compositions are effective for solubilizing therapeutic agents, particularly difficulty soluble therapeutic agents. The compositions advantageously enhance the bioavailability of the therapeutic agents. The invention also provides therapeutic agent formulations based on the compositions that are effective for the delivery of therapeutic agents, particularly oral administration of therapeutic agents. Amphotericin B formulations are used herein as the prototypic example, however, one of skill in the art will appreciate that such formulations are applicable to a variety of therapeutic agents. Accordingly, in one aspect, the invention provides amphotericin B formulations based on the compositions. The amphotericin B formulations effectively solubilize amphotericin B providing formulations having increased amphotericin B concentrations and, at the same time, provide for enhanced amphotericin B bioavailability.

Amphotericin B Formulations

In one aspect, the present invention provides amphotericin B formulations, methods for making the formulations, methods for administering amphotericin B using the formulations, and methods for treating diseases treatable by amphotericin B by administering the formulations.

Amphotericin B is an effective antifungal agent, and at present, is the drug of choice for treating most serious systemic fungal infections. The drug binds strongly to ergosterol, a major sterol component of fungal membranes, forming pores in the membranes causing disruption of the membrane, cell permeability, and lysis.

Amphotericin B has had limitations in clinical administration due to several unfavorable properties. First, amphotericin B has a strong binding affinity for cholesterol, a sterol present in most mammalian cell membranes, and therefore is capable of disrupting host cells. This leads to renal toxicity of the drug. Second, amphotericin B is not absorbed in the gastrointestinal tract (GIT) due to its poor solubility and its sensitivity to the acid environment of the stomach. To overcome this problem, amphotericin B is used parenterally as liposomal (AMBISOME®) or as colloidal dispersion (FUNGIZONE®, ABELCET®) for the treatment of certain systemic fungal infections (Arikan and Rex, 2001. Lipid-based antifungal agents: current status. *Curr. Pharm. Des.* 5, 393-415).

However, intravenous injection and infusion of amphotericin B have significant disadvantages. First, the intravenous injection and infusion of amphotericin B has been associated with considerable fluctuation of drug concentrations in the blood and side effects such as nephrotoxicity (Müller et al., 2000, Nanosuspensions for the formulation of poorly soluble drugs-rationale for development and what we can expect for the future. In: Nielloud, F., Marti-Mestres, G. (Eds.), Pharmaceutical emulsions and suspensions. Plenum Press/Marcel Dekker, New York, pp. 383-408). Second, in addition to the high cost, the injection and infusion formulation of amphotericin B have also presented low compliance and technical problems with administration in endemic countries.

In one embodiment, the present invention overcomes these disadvantages by providing an amphotericin B formulation that can be administered orally. The oral amphotericin B formulations of the invention can be expected to improve patient compliance and to improve pharmacokinetics of the drug and to increase the amphotericin B absorption in GI track.

Amphotericin B is an antimycotic polyene antibiotic obtained from *Streptomyces nodosus* M4575. Amphotericin B is designated chemically as [1R-(1R*,3S*,5R*,6R*,9R*,11R*,15S*,16R*,17R*,18S*,19E,21E,23E,25E,27E,29E,31E,33R*,35S*,36R*,37S,)]-33-[(3-amino-3,6-dideoxy-β-D-mannopyranosyl)oxy]1,3,5,6,9,11,17,37-octahydroxy-15,16,18-trimethyl-13-oxo-14,39-dioxabicyclo-[33.3.1]nonatriaconta-19,21,23,25,27,29,31-heptaene-36-carboxylic acid. The chemical structure of amphotericin B is shown in FIG. 1A. Crystalline amphotericin B is insoluble in water.

In one aspect, the present invention provides amphotericin B formulations. The amphotericin formulations of the invention include
  (a) amphotericin B;
  (b) one or more fatty acid glycerol esters; and
  (c) one or more polyethylene oxide-containing phospholipids or one or more polyethylene oxide-containing fatty acid esters.

In representative formulations, amphotericin B is present in an amount from about 0.5 to about 10 mg/mL of the formulation. In one embodiment, amphotericin B or pharmaceutically acceptable salt thereof is present in the formulation in about 5 mg/mL. In one embodiment, amphotericin B or its pharmaceutically acceptable salt thereof is present in the formulation in about 7 mg/mL.

The amphotericin B formulations include one or more fatty acid glycerol esters, and typically, a mixture of fatty acid glycerol esters. As used herein the term "fatty acid glycerol esters" refers to esters formed between glycerol and one or more fatty acids including mono-, di-, and tri-esters (i.e., glycerides). Suitable fatty acids include saturated and unsaturated fatty acids having from eight (8) to twenty-two (22) carbons atoms (i.e., C8-C22 fatty acids). In certain embodiments, suitable fatty acids include C12-C18 fatty acids.

The fatty acid glycerol esters useful in the formulations can be provided by commercially available sources. A representative source for the fatty acid glycerol esters is a mixture of mono-, di-, and triesters commercially available as PECEOL® (Gattefosse, Saint Priest Cedex, France), commonly referred to as "glyceryl oleate" or "glyceryl monooleate." When PECEOL® is used as the source of fatty acid glycerol esters in the formulations, the fatty acid glycerol esters comprise from about 32 to about 52% by weight fatty acid monoglycerides, from about 30 to about 50% by weight fatty acid diglycerides, and from about 5 to about 20% by weight fatty acid triglycerides. The fatty acid glycerol esters comprise greater than about 60% by weight oleic acid (C18:1) mono-, di-, and triglycerides. Other fatty acid glycerol esters include esters of palmitic acid (C16) (less than about 12%), stearic acid (C18) (less than about 6%), linoleic acid (C18:2) (less than about 35%), linolenic aid (C18:3) (less than about 2%), arachidic acid (C20) (less than about 2%), and eicosenoic acid (C20:1) (less than about 2%). PECEOL® can also include free glycerol (typically about 1%). In one embodiment, the fatty acid glycerol esters comprise about 44% by weight fatty acid monoglycerides, about 45% by weight fatty acid diglycerides, and about 9% by weight fatty acid triglycerides, and the fatty acid glycerol esters comprise about 78% by weight oleic acid (C18:1) mono-, di-, and triglycerides. Other fatty acid glycerol esters include esters of palmitic acid (C16) (about 4%), stearic acid (C18) (about 2%), linoleic acid (C18:2) (about 12%), linolenic aid (C18:3) (less than 1%), arachidic acid (C20) (less than 1%), and eicosenoic acid (C20:1) (less than 1%).

In certain embodiments, the formulations of the invention can include glycerol in an amount less than about 10% by weight.

Amphotericin B Formulations: Polyethylene Oxide-Containing Phospholipids (DSPE-PEGs).

The amphotericin B formulations include one or more polyethoxylated lipids. In one embodiment, the polyethoxylated lipids are polyethylene oxide-containing phospholipids, or a mixture of polyethylene oxide-containing phospholipids. In another embodiment, the polyethoxylated lipids are polyethylene oxide-containing fatty acid esters, or a mixture of polyethylene oxide-containing fatty acid esters.

Accordingly, in one embodiment, the amphotericin B formulations of the invention include
(a) amphotericin B;
(b) one or more fatty acid glycerol esters; and
(c) one or more polyethylene oxide-containing phospholipids.

As used herein, the term "polyethylene oxide-containing phospholipid" refers to a phospholipid that includes a polyethylene oxide group (i.e., polyethylene glycol group) covalently coupled to the phospholipid, typically through a carbamate or an ester bond. Phospholipids are derived from glycerol and can include a phosphate ester group and two fatty acid ester groups. Suitable fatty acids include saturated and unsaturated fatty acids having from eight (8) to twenty-two (22) carbons atoms (i.e., C8-C22 fatty acids). In certain embodiments, suitable fatty acids include saturated C12-C18 fatty acids. Representative polyethylene oxide-containing phospholipids include C8-C22 saturated fatty acid esters of a phosphatidyl ethanolamine polyethylene glycol salt. In certain embodiments, suitable fatty acids include saturated C12-C18 fatty acids.

The molecular weight of the polyethylene oxide group of the polyethylene oxide-containing phospholipid can be varied to optimize the solubility of the therapeutic agent (e.g., amphotericin B) in the formulation. Representative average molecular weights for the polyethylene oxide groups can be from about 200 to about 5000 (e.g., PEG 200 to PEG 5000).

In one embodiment, the polyethylene oxide-containing phospholipids are distearoyl phosphatidyl ethanolamine polyethylene glycol salts. Representative distearoylphosphatidyl ethanolamine polyethylene glycol salts include distearoylphosphatidyl ethanolamine polyethylene glycol 350 (DSPE-PEG-350) salts, distearoylphosphatidyl ethanolamine polyethylene glycol 550 (DSPE-PEG-550) salts, distearoylphosphatidyl ethanolamine polyethylene glycol 750 (DSPE-PEG-750) salts, distearoylphosphatidyl ethanolamine polyethylene glycol 1000 (DSPE-PEG-1000) salts, distearoylphosphatidyl ethanolamine polyethylene glycol 1500 (DSPE-PEG-1500) salts, and distearoylphosphatidyl ethanolamine polyethylene glycol 2000 (DSPE-PEG-2000) salts. Mixtures can also be used. For the distearoylphosphatidyl ethanolamine polyethylene glycol salts above, the number (e.g., 350, 550, 750, 1000, and 2000) designates the average molecular weight of the polyethylene oxide group. The abbreviations for these salts used herein is provided in parentheses above.

Suitable distearoylphosphatidyl ethanolamine polyethylene glycol salts include ammonium and sodium salts.

Figure 1B:
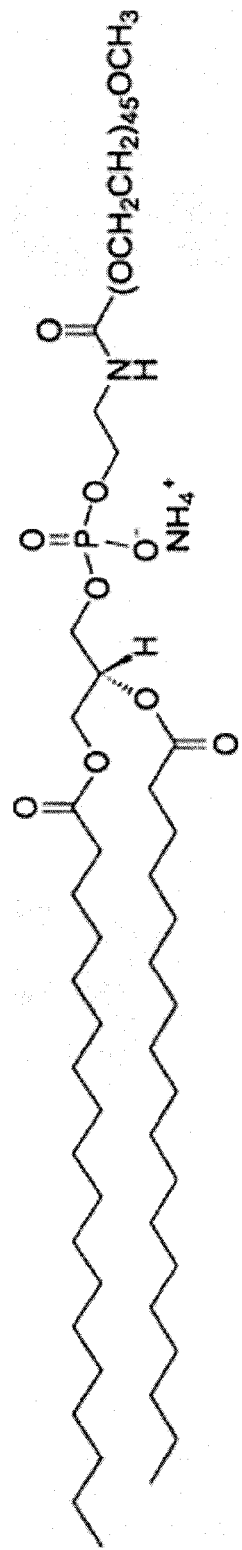
FIG. 1B illustrates the chemical structure of distearoylphosphatidyl ethanolamine polyethylene glycol 2000 ammonium salt (DSPE-PEG-2000).

The chemical structure of distearoylphosphatidyl ethanolamine polyethylene glycol 2000 (DSPE-PEG-2000) ammonium salt is illustrated in FIG. 1B. Referring to FIG. 1B, the polyethylene oxide-containing phospholipid includes a phosphate ester group and two fatty acid ester (stearate) groups, and a polyethylene oxide group covalently coupled to the amino group of the phosphatidyl ethanolamine through a carbamate bond.

As noted above, the polyethylene oxide-containing phospholipid affects the ability of the formulation to solubilize a therapeutic agent. In general, the greater the amount of polyethylene oxide-containing phospholipid, the greater the solubilizing capacity of the formulation for difficulty soluble therapeutic agents. The polyethylene oxide-containing phospholipid can be present in the formulation in an amount from about 1 mM to about 30 mM based on the volume of the formulation. In certain embodiments, the distearoylphosphatidyl ethanolamine polyethylene glycol salt is present in the formulation in an amount from 1 mM to about 30 mM based on the volume of the formulation. In one embodiment, the distearoylphosphatidyl ethanolamine polyethylene glycol salt is present in the formulation in about 15 mM based on the volume of the formulation.

Figure 2:
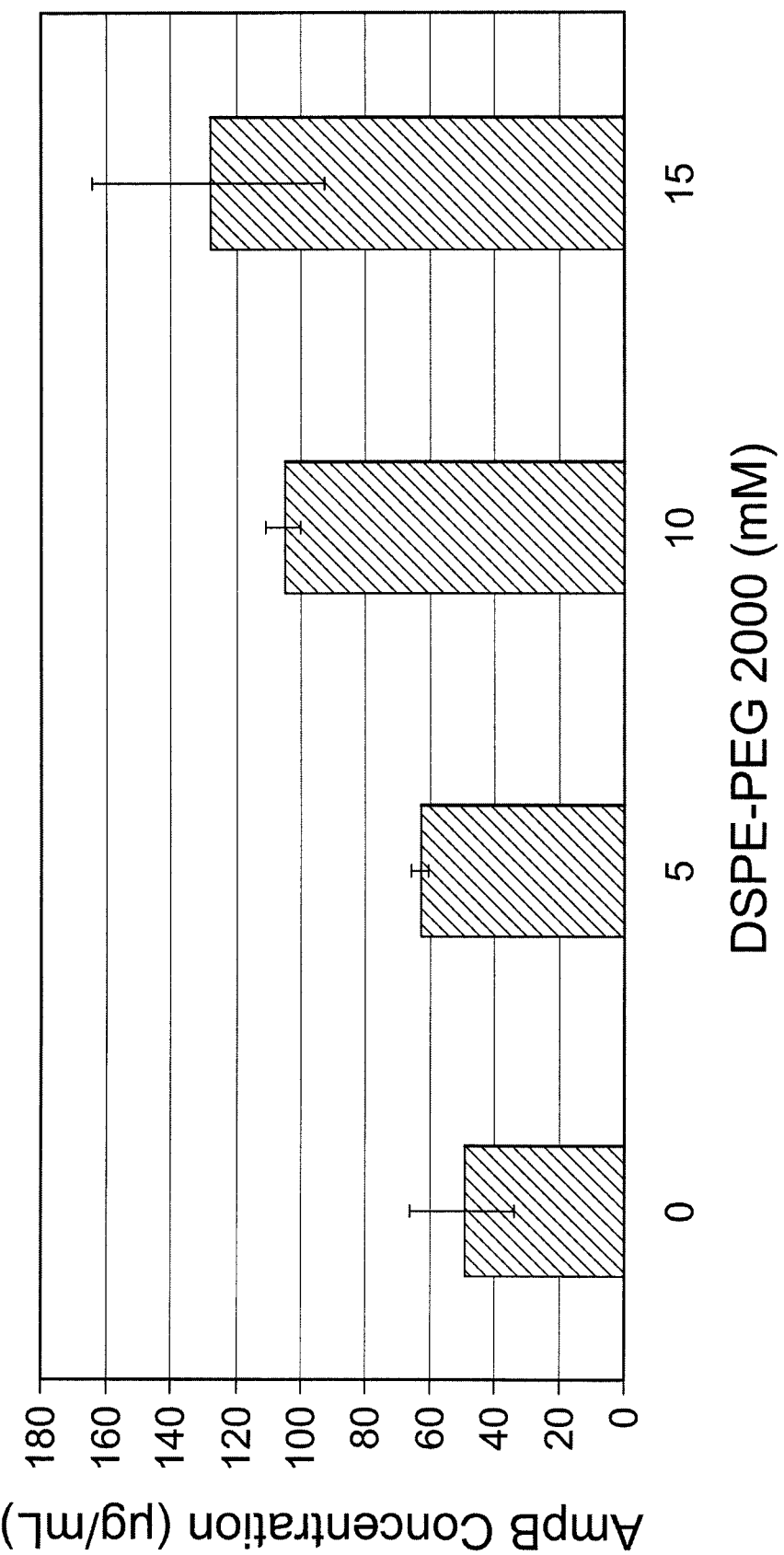
FIG. 2 compares AmpB concentration (μg/mL) in an AmpB/PECEOL® formulation and representative AmpB formulations of the invention (AmpB/PECEOL®/DSPE-PEG-2000) containing DSPE-PEG-2000 at concentrations of 5, 10, and 15 mM.

FIG. 2 compares amphotericin B concentration ($\mu g/mL$) in an AmpB/PECEOL® formulation (containing no polyethylene oxide-containing phospholipids or polyethylene oxide-containing fatty acid esters) and representative AmpB formulations of the invention (AmpB/PECEOL®/DSPE-PEG-2000) containing DSPE-PEG-2000 at concentrations of 5, 10, and 15 mM. AmpB measured by UV absorbance of centrifuged samples after 24 hrs at 45° C.

In one embodiment, the amphotericin B formulations of the invention include
(a) amphotericin B;
(b) oleic acid glycerol esters; and
(c) a distearoylphosphatidyl ethanolamine polyethylene glycol salt.

In one embodiment, the amphotericin B formulation of the invention includes amphotericin B, PECEOL®, and a distearoylphosphatidyl ethanolamine polyethylene glycol salt. In this embodiment, the distearoylphosphatidyl ethanolamine polyethylene glycol salt is present in an amount up to about 30 mM.

The preparation and characterization of representative amphotericin B formulations of the invention that include polyethylene oxide-containing phospholipids is described in Example 1.

The amphotericin B formulations that include polyethylene oxide-containing phospholipids include amphotericin B that is both partially solubilized (dissolved) and present as solid particles to provide a fine solid dispersion. Dispersion of the formulation in aqueous media provides a nano-/microemulsion having emulsion droplets that range in size from about 50 nm to about 5 $\mu m$.

Polyethylene glycol molecular weight had no clear effect on the emulsion droplet size in simulated intestinal fluid (Table 3) following mixing over a period of 2 h at 37° C. Submicron mean diameters were observed in the range of 300-600 nm with a fairly wide polydispersity. A bimodal particle size distribution was also generated, with a small subpopulation (about 20%) centered in submicron range (150-300 nm) and another centered in the 1-2 $\mu m$ range (about 80%). AmpB in PECEOL® alone also formed droplets of similar size and distribution in simulated intestinal fluid.

Figure 3A:
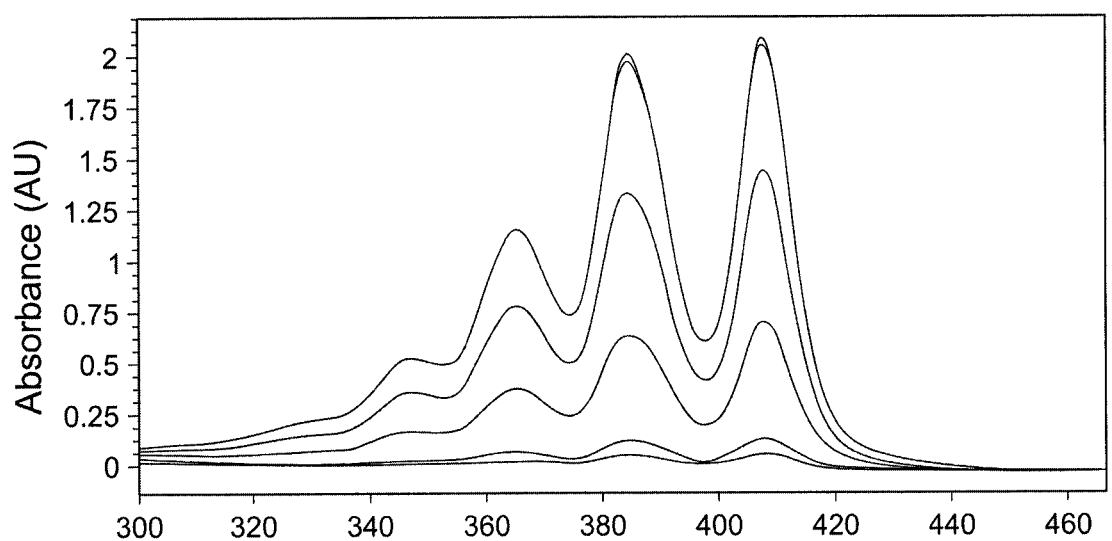
FIG. 3A compares the UV absorbance spectra over time of representative AmpB formulations of the invention (PECEOL®/DSPE-PEG) at various concentrations (0.5-15 μg/ml) incubated in simulated gastric fluid (SGF).
Figure 3B:
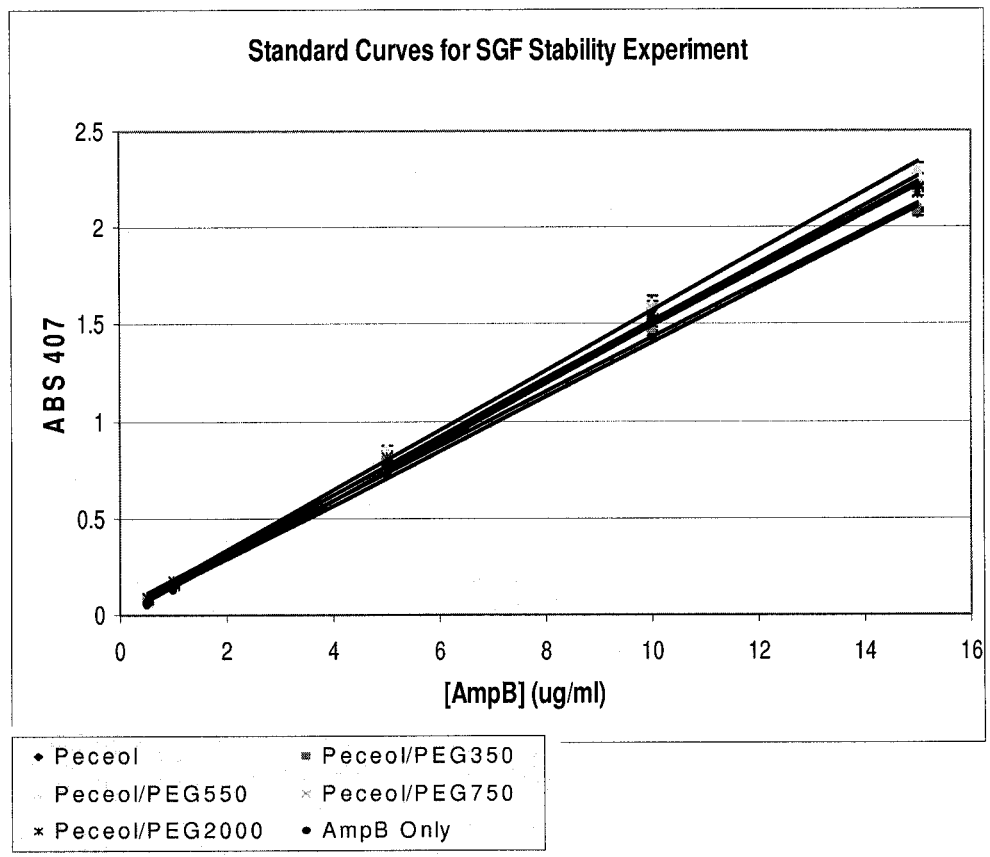
FIG. 3B compares standard curves from the data in FIG. 2A combined using peak height at 407 nm to construct the standard curves of AmpB absorbance vs. concentration. A different standard curve was prepared for each formulation where DSPE-PEG molecular weight varied.
Figure 4:
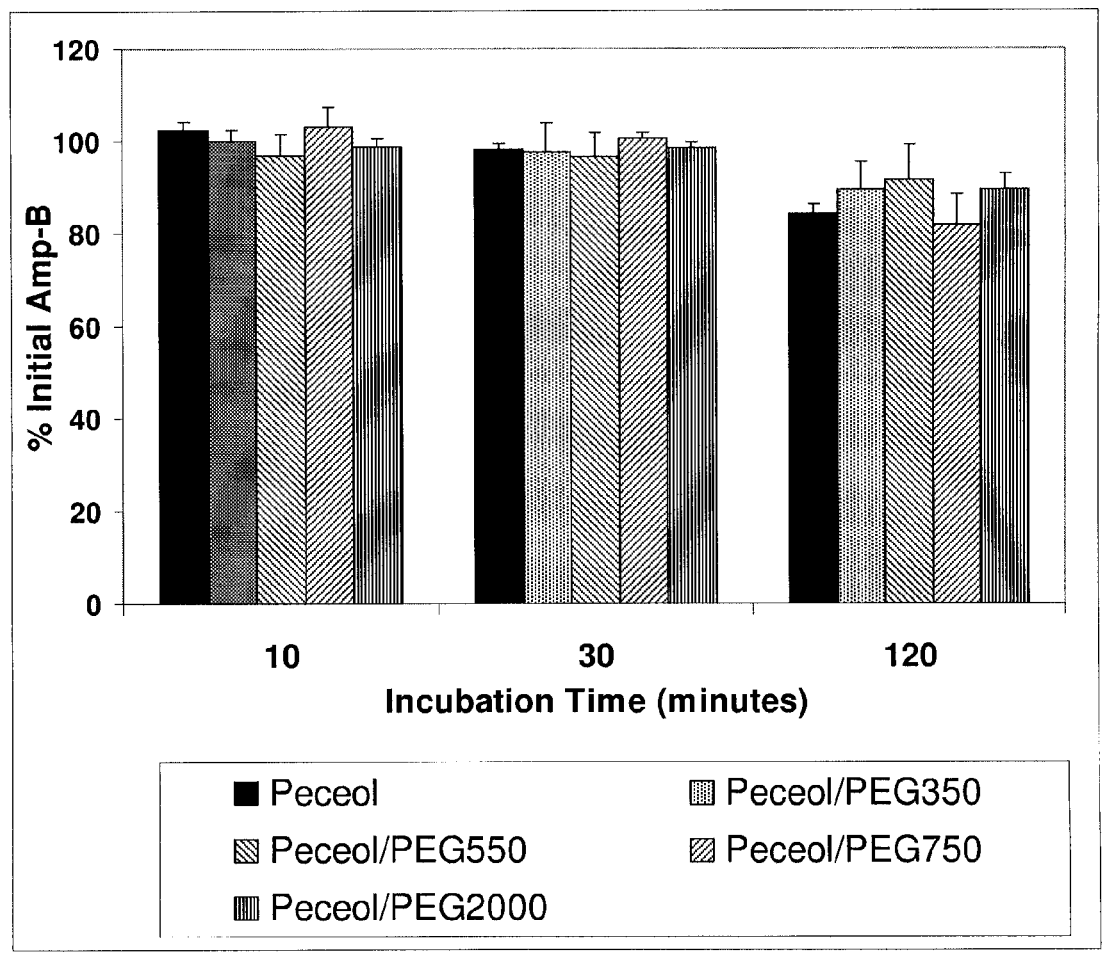
FIG. 4 compares the stability of AmpB in representative formulations of the invention (PECEOL®/DSPE-PEG 350, 550, 750, and 2000) with an AmpB/PECEOL® formulation at 37° C. in simulated gastric fluid as a function of time (10, 30, and 120 min).

To determine their effectiveness as orally administered formulations, the stability of representative amphotericin B formulations of the invention was evaluated in simulated gastric fluid. FIG. 3A compares the UV absorbance spectra over time of representative AmpB formulations of the invention (PECEOL®/DSPE-PEG) at various concentrations (0.5-15 µg/ml) incubated in simulated gastric fluid (SGF). There is no change in the peak height or peak ratio at any concentration as a function of incubation time up to 60 min. FIG. 3B compares standard curves from the data in FIG. 2A combined using peak height at 407 nm to construct the standard curves of AmpB absorbance vs. concentration. A different standard curve was prepared for each formulation where DSPE-PEG molecular weight varied. FIG. 4 compares the stability of AmpB in representative formulations of the invention (PECEOL®/DSPE-PEG 350, 550, 750, and 2000) with an AmpB/PECEOL® formulation at 37° C. in simulated gastric fluid as a function of time (10, 30, and 120 min). Data represent the mean±SD of three independent experiments, each of which was performed in triplicate. Each of the evaluated representative formulations of the invention demonstrated stability in simulated gastric fluid over the time period evaluated.

Figure 5A:
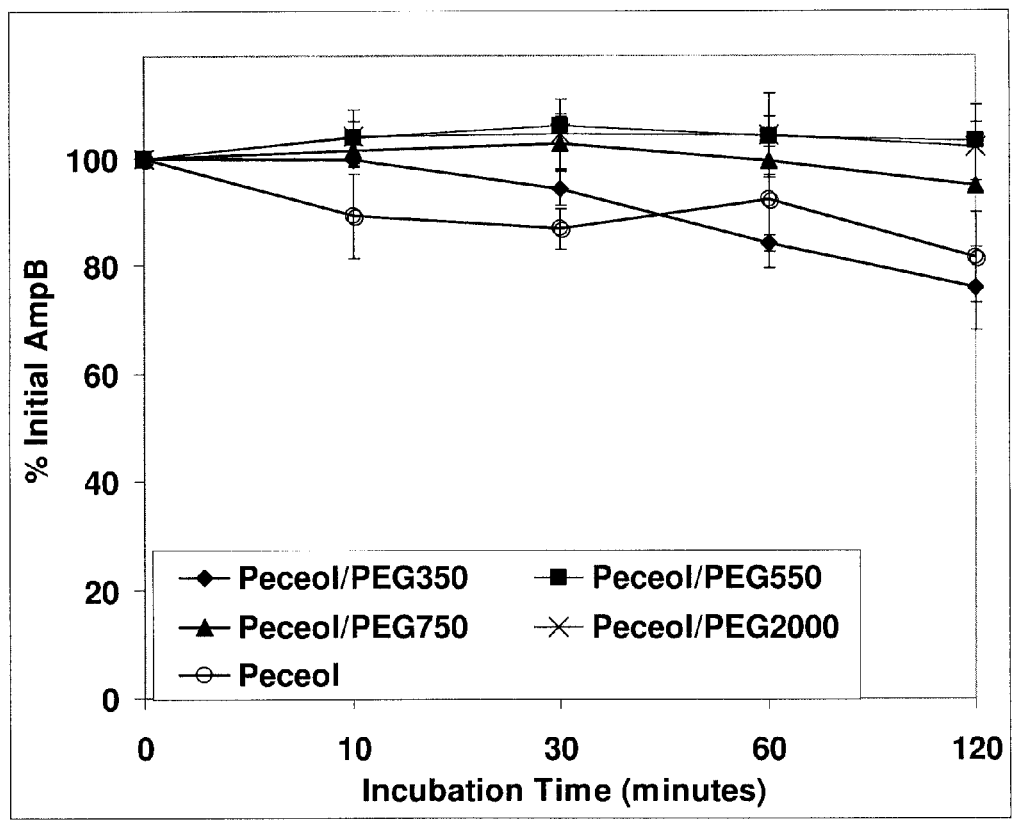
FIGS. 5A and 5B compare the stability of AmpB in representative formulations of the invention (PECEOL®/DSPE-PEG 350, 550, 750, and 2000, designated PEG 350, 550, 750, 2000, respectively) with an AmpB/PECEOL® formulation at 37° C. in fasted-state simulated intestinal fluid (FSSIF) without lecithin (5A) and with lecithin (5B) as a function of time (10, 30, 60, and 120 min).
Figure 5B:
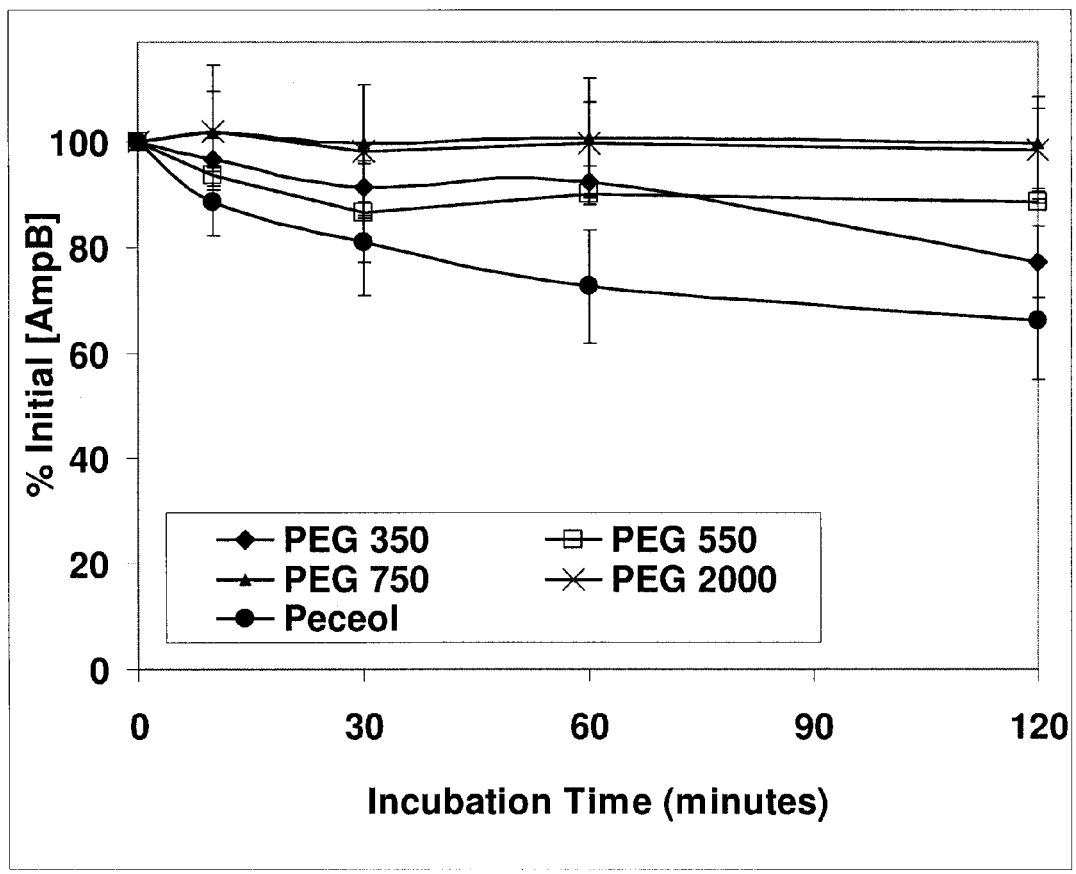
Figure 6:
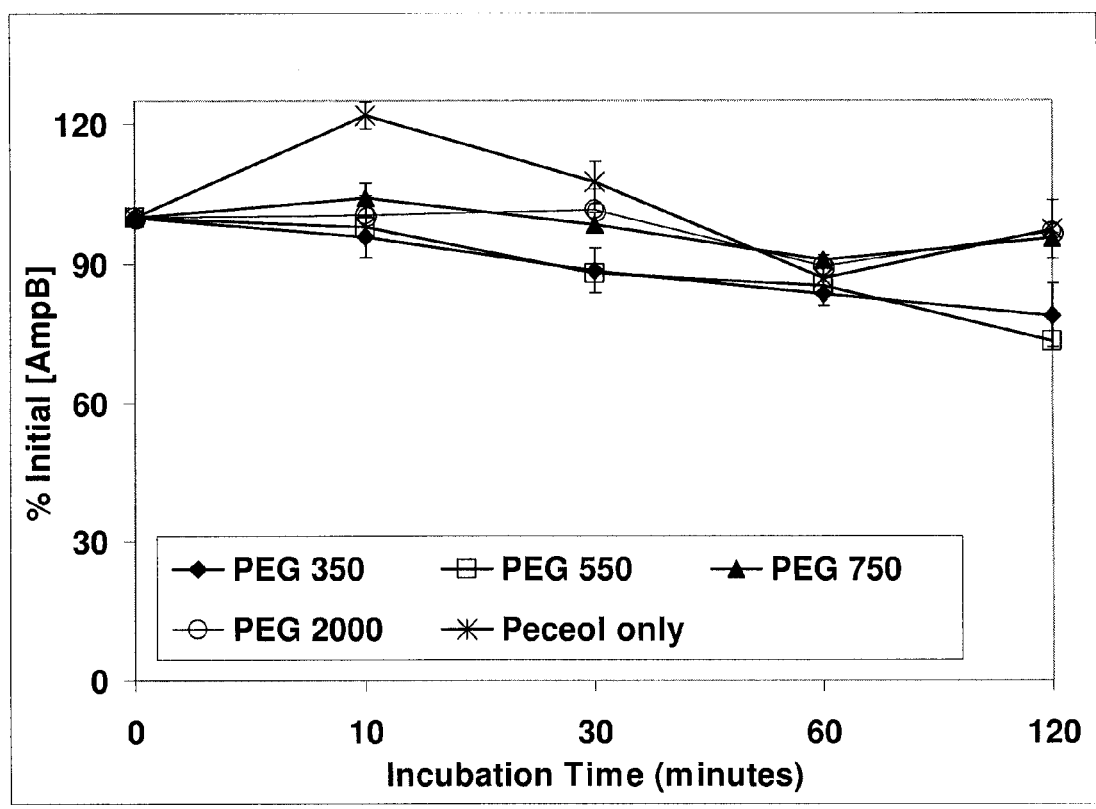
FIG. 6 compares the stability of AmpB in representative formulations of the invention (PECEOL®/DSPE-PEG 350, 550, 750, and 2000, designated PEG 350, 550, 750, 2000, respectively) with an AmpB/PECEOL® formulation at 37° C. in simulated intestinal fluid (SIF) with pancreatin enzymes as a function of time (10, 30, 60, and 120 min).

The stability of representative amphotericin B formulations of the invention was also evaluated in fasted-state simulated intestinal fluid (FSSIF) without lecithin and with lecithin, and in simulated intestinal fluid with pancreatin enzymes. FIGS. 5A and 5B compare the stability of AmpB in representative formulations of the invention (PECEOL®/DSPE-PEG 350, 550, 750, and 2000, designated PEG 350, 550, 750, 2000, respectively) with an AmpB/PECEOL® formulation at 37° C. in fasted-state simulated intestinal fluid (FSSIF) without lecithin (5A) and with lecithin (5B) as a function of time (10, 30, 60, and 120 min). Data represent the mean±SD of three independent experiments, each of which was performed in triplicate. FIG. 6 compares the stability of AmpB in representative formulations of the invention (PECEOL®/DSPE-PEG 350, 550, 750, and 2000, designated PEG 350, 550, 750, 2000, respectively) with an AmpB/PECEOL® formulation at 37° C. in simulated intestinal fluid (SIF) with pancreatin enzymes as a function of time (10, 30, 60, and 120 min) Data represent the mean±SD of three independent experiments, each of which was performed in triplicate. Each of the evaluated representative formulations of the invention demonstrated stability in the simulated intestinal fluids over the time period evaluated.

The stability of the representative amphotericin B formulations in the GI fluids demonstrates their suitability as orally administered formulations.

AmpB in PECEOL® was stabilized and its solubility enhanced 50-fold by the incorporation of 15 mM DSPE-PEG, where the PEG mean molecular weight was varied between 350 and 2000. Drug stability in stomach and intestine is critical for promoting drug absorption in the GI tract. AmpB is well known to be more soluble but relatively unstable at low pH, therefore any protection afforded by the lipid components of the formulation could be a significant benefit toward increasing the oral bioavailability of AmpB. It is also important to know if the lipidic vehicles influenced the superaggregation state of AmpB, which has been previously been shown to influence drug solubility as well as in vivo activity. The UV spectral pattern of AmpB in the lipidic vehicles described herein was consistent with monomeric AmpB before and after incubation in simulated gastric or intestinal fluids (see FIG. 3A). No UV spectral pattern change was noted upon ambient temperature storage (21° C.) over a period of 4 weeks either (data not shown). However, interactions between the AmpB and the lipid components in the undiluted formulation (in the absence of the assay solvent) or following oral absorption in vivo may be different.

Stability of representative formulations of the invention in simulated gastric fluid over 2 h was excellent, with surprisingly little variability between formulations prepared with the various DSPE-PEGs or with only PECEOL® (see FIGS. 4-6). All showed a translucent appearance with no precipitate appearing. More variation in stability was observed in simulated fasted-state intestinal fluid containing bile salts (see FIGS. 5A and 5B). The emulsification properties of the bile salts, lecithin and phospholipase in pancreatin could influence formulation stability and therefore drug stability was evaluated in simulated intestinal fluids containing these components. Lecithin would likely be incorporated into the lipid mixture when including in the simulated intestinal fluid, which had the potential to either improve the association of amphotericin B with the lipid excipients or to exclude it. The presence of lecithin, however, made no appreciable difference in the rate or extent of degradation or in the rank order of degradation at the end of 2 h (see FIG. 5B). Clearly, DSPE-PEG 350 containing formulations provided less drug stability than those containing the longer-chain PEGs. In the absence of lecithin, submicron particle size analysis did not show a significant population below 50 nm that would be consistent with DSPE-PEG micelles, e.g., if DSPE-PEG350 had self-associated into a separate micelle population (see FIG. 5A). Furthermore, there was no significant effect on particle size due to the presence of DSPE-PEG or polyethylene glycol molecular weight, suggesting that the emulsification properties are largely derived from the PECEOL® component. However, the possibility that a small fraction of micelles exists in equilibrium with the lipid excipient/drug mixture in the simulated intestinal fluid cannot be excluded for any of the DSPE-PEG formulations, however, it does not appear to be a major component. Therefore, it is possible that the improved stability of AmpB in PECEOL®/DSPE-PEG of higher molecular weight may be related to the surface properties of the emulsion droplets themselves, in spite of the lack of a direct relationship to particle size distribution, such that the hydrophilic polyethylene glycol chains may orient to the water interface while the PECEOL®/AmpB fraction would remain in the inner oil phase and thereby sequestering and protecting the AmpB from degradation. Thus, there was a trend to increased stability for PEG molecular weight 750 and 2000 compared to 350 and 550. The interactions between AmpB and the PECEOL®/DSPE-PEG resulted in a UV spectral shape consistent with monomeric AmpB rather than aggregated AmpB (FIG. 3A).

Amphotericin B Formulations: Polyethylene Oxide-Containing Fatty Acid Esters.

As noted above, the amphotericin B formulations include one or more polyethoxylated lipids such as polyethylene oxide-containing phospholipids or one or more polyethylene oxide-containing fatty acid esters, and typically, a mixture of polyethylene oxide-containing phospholipids or a mixture of polyethylene oxide-containing fatty acid esters.

Accordingly, in one embodiment, the amphotericin B formulations of the invention include
  (a) amphotericin B;
  (b) one or more fatty acid glycerol esters; and
  (c) one or more polyethylene oxide-containing fatty acid esters.

As used herein, the term "polyethylene oxide-containing fatty acid ester" refers to a fatty acid ester that includes a polyethylene oxide group (i.e., polyethylene glycol group) covalently coupled to the fatty acid through an ester bond. Polyethylene oxide-containing fatty acid esters include mono- and di-fatty acid esters of polyethylene glycol. Suitable polyethylene oxide-containing fatty acid esters are derived from fatty acids including saturated and unsaturated fatty acids having from eight (8) to twenty-two (22) carbons atoms (i.e., a polyethylene oxide ester of a C8-C22 fatty acid). In certain embodiments, suitable polyethylene oxide-containing fatty acid esters are derived from fatty acids including saturated and unsaturated fatty acids having from twelve (12) to eighteen (18) carbons atoms (i.e., a polyethylene oxide ester of a C12-C18 fatty acid). Representative polyethylene oxide-containing fatty acid esters include saturated C8-C22 fatty acid esters. In certain embodiments, suitable polyethylene oxide-containing fatty acid esters include saturated C12-C18 fatty acids.

The molecular weight of the polyethylene oxide group of the polyethylene oxide-containing fatty acid ester can be varied to optimize the solubility of the therapeutic agent (e.g., amphotericin B) in the formulation. Representative average molecular weights for the polyethylene oxide groups can be from about 350 to about 2000. In one embodiment, the average molecular weight for the polyethylene oxide group is about 1500.

In this embodiment, the amphotericin B formulations include one or more polyethylene oxide-containing fatty acid esters, and typically, a mixture of polyethylene oxide-containing fatty acid esters (mono- and di-fatty acid esters of polyethylene glycol).

The polyethylene oxide-containing fatty acid esters useful in the formulations can be provided by commercially available sources. Representative polyethylene oxide-containing fatty acid esters (mixtures of mono- and diesters) are commercially available under the designation GELUCIRE® (Gattefosse, Saint Priest Cedex, France). Suitable polyethylene oxide-containing fatty acid esters can be provided by GELUCIRE® 44/14, GELUCIRE® 50/13, and GELUCIRE® 53/10. The numerals in these designations refer to the melting point and hydrophilic/lipophilic balance (HLB) of these materials, respectively.

GELUCIRE® 44/14, GELUCIRE® 50/13, and GELUCIRE® 53/10 are mixtures of (a) mono-, di-, and triesters of glycerol (glycerides) and (b) mono- and diesters of polyethylene glycol (macrogols). The GELUCIRES can also include free polyethylene glycol (e.g., PEG 1500).

Lauric acid (C12) is the predominant fatty acid component of the glycerides and polyethylene glycol esters in GELUCIRE® 44/14. GELUCIRE® 44/14 is referred to as a mixture of glyceryl dilaurate (lauric acid diester with glycerol) and PEG dilaurate (lauric acid diester with polyethylene glycol), and is commonly known as PEG-32 glyceryl laurate (Gattefosse) lauroyl macrogol-32 glycerides EP, or lauroyl polyoxylglycerides USP/NF. GELUCIRE® 44/14 is produced by the reaction of hydrogenated palm kernel oil with polyethylene glycol (average molecular weight 1500). GELUCIRE® 44/14 includes about 20% mono-, di- and, triglycerides, about 72% mono- and di-fatty acid esters of polyethylene glycol 1500, and about 8% polyethylene glycol 1500.

GELUCIRE® 44/14 includes lauric acid (C12) esters (30 to 50%), myristic acid (C14) esters (5 to 25%), palmitic acid (C16) esters (4 to 25%), stearic acid (C18) esters (5 to 35%), caprylic acid (C8) esters (less than 15%), and capric acid (C10) esters (less than 12%). GELUCIRE® 44/14 may also include free glycerol (typically less than about 1%). In a representative formulation, GELUCIRE® 44/14 includes lauric acid (C12) esters (about 47%), myristic acid (C14) esters (about 18%), palmitic acid (C16) esters (about 10%), stearic acid (C18) esters (about 11%), caprylic acid (C8) esters (about 8%), and capric acid (C10) esters (about 12%).

Palmitic acid (C16) (40-50%) and stearic acid (C18) (48-58%) are the predominant fatty acid components of the glycerides and polyethylene glycol esters in GELUCIRE® 50/13. GELUCIRE® 50/13 is known as PEG-32 glyceryl palmitostearate (Gattefosse), stearoyl macrogolglycerides EP, or stearoyl polyoxylglycerides USP/NF. GELUCIRE® 50/13 includes palmitic acid (C16) esters (40 to 50%), stearic acid (C18) esters (48 to 58%) (stearic and palmitic acid esters greater than about 90%), lauric acid (C12) esters (less than 5%), myristic acid (C14) esters (less than 5%), caprylic acid (C8) esters (less than 3%), and capric acid (C10) esters (less than 3%). GELUCIRE® 50/13 may also include free glycerol (typically less than about 1%). In a representative formulation, GELUCIRE® 50/13 includes palmitic acid (C16) esters (about 43%), stearic acid (C18) esters (about 54%) (stearic and palmitic acid esters about 97%), lauric acid (C12) esters (less than 1%), myristic acid (C14) esters (about 1%), caprylic acid (C8) esters (less than 1%), and capric acid (C10) esters (less than 1%)

Stearic acid (C18) is the predominant fatty acid component of the glycerides and polyethylene glycol esters in GELUCIRE® 53/10. GELUCIRE® 53/10 is known as PEG-32 glyceryl stearate (Gattefosse).

In one embodiment, the polyethylene oxide-containing fatty acid ester is a lauric acid ester, a palmitic acid ester, or a stearic acid ester (i.e., mono- and di-lauric acid esters of polyethylene glycol, mono- and di-palmitic acid esters of polyethylene glycol, mono- and di-stearic acid esters of polyethylene glycol). Mixtures of these esters can also be used.

For embodiments that include polyethylene oxide-containing fatty acid esters, the ratio of the fatty acid glycerol esters to polyethylene oxide-containing fatty acid esters is from about 20:80 to about 80:20 v/v. In one embodiment, the ratio of the fatty acid glycerol esters to polyethylene oxide-containing fatty acid esters is about 30:70 v/v. In one embodiment, the ratio of the fatty acid glycerol esters to polyethylene oxide-containing fatty acid esters is about 40:60 v/v. In one embodiment, the ratio of the fatty acid glycerol esters to polyethylene oxide-containing fatty acid esters is about 50:50 v/v. In one embodiment, the ratio of the fatty acid glycerol esters to polyethylene oxide-containing fatty acid esters is about 60:40 v/v. In one embodiment, the ratio of the fatty acid glycerol esters to polyethylene oxide-containing fatty acid esters is about 70:30 v/v.

In one embodiment, the amphotericin B formulations of the invention include
  (a) amphotericin B;
  (b) oleic acid glycerol esters; and
  (c) lauric acid esters of polyethylene glycol.
In another embodiment, the amphotericin B formulations of the invention include
  (a) amphotericin B;
  (b) oleic acid glycerol esters; and
  (c) palmitic and stearic acid esters of polyethylene glycol.
In a further embodiment, the amphotericin B formulations of the invention include
  (a) amphotericin B;
  (b) oleic acid glycerol esters; and
  (c) stearic acid esters of polyethylene glycol.

In one embodiment, the amphotericin B formulation of the invention includes amphotericin B, PECEOL®, and GELUCIRE® 44/14. In another embodiment, the amphotericin B formulation of the invention includes amphotericin B, PECEOL®, and GELUCIRE® 50/13. In a further embodiment, the amphotericin B formulation of the invention includes amphotericin B, PECEOL®, and GELUCIRE® 53/10. In these embodiments, the ratio of PECEOL® to GELUCIRE® can be from 20:80 to 80:20 (e.g., 20:80, 30:70; 40:60; 50:50; 60:40; 70:30; and 80:20).

The preparation and characterization of representative amphotericin B formulations of the invention that include polyethylene oxide-containing fatty acid esters is described in Example 1.

The amphotericin B formulations that include polyethylene oxide-containing fatty acid esters include amphotericin B that is both partially solubilized (dissolved) and present as solid particles to provide a fine solid dispersion. Dispersion of the formulations in aqueous media provides a nano-/microemulsion.

The preliminary SEDDS formulations of amphotericin B (see Example 1) did produce self-emulsification and a small droplet size upon dispersion into physiological saline. The dispersion properties of the CAPTEX® 355-based formulations were similar to those based on mixtures of PECEOL®/GELUCIRE® 44/14 or 50/13, generating multiple subpopulations of emulsion droplets in the submicron or 1 μm range (see Tables 1 and 2). This particle size would be appropriate for dispersing the drug in the GI tract to best facilitate absorption.

Figure 10A:
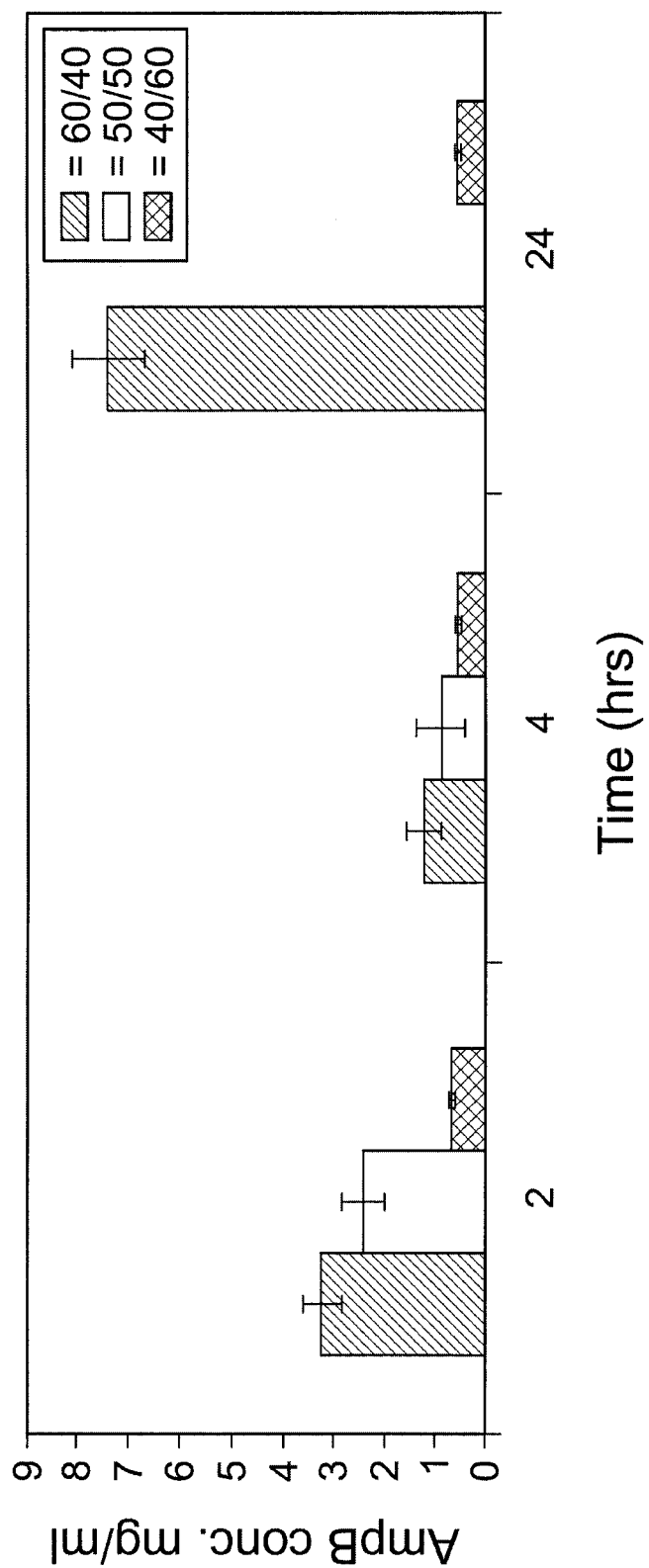
FIGS. 10A, 10B, and 10C compare AmpB concentration (mg/mL) in representative AmpB formulations of the invention (AmpB/PECEOL®/GELUCIRE® 44/14; AmpB/PECEOL®/GELUCIRE® 50/13; and AmpB/PECEOL®/GELUCIRE® 53/10) at varying ratios of PECEOL®:GELUCIRE® (60:40; 50:50; and 40:60 v/v) at 2, 4 and 24 hrs.
Figure 10B:
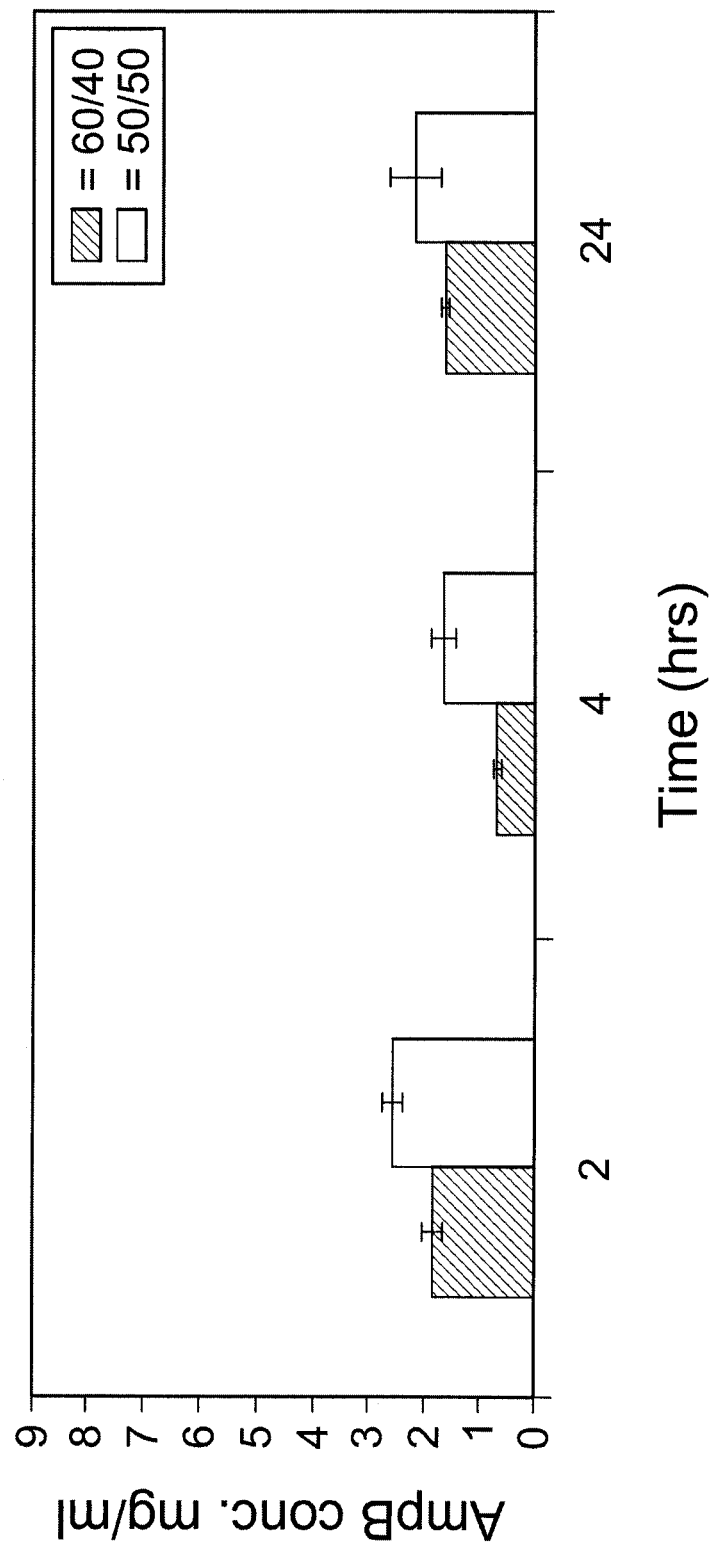
Figure 10C:
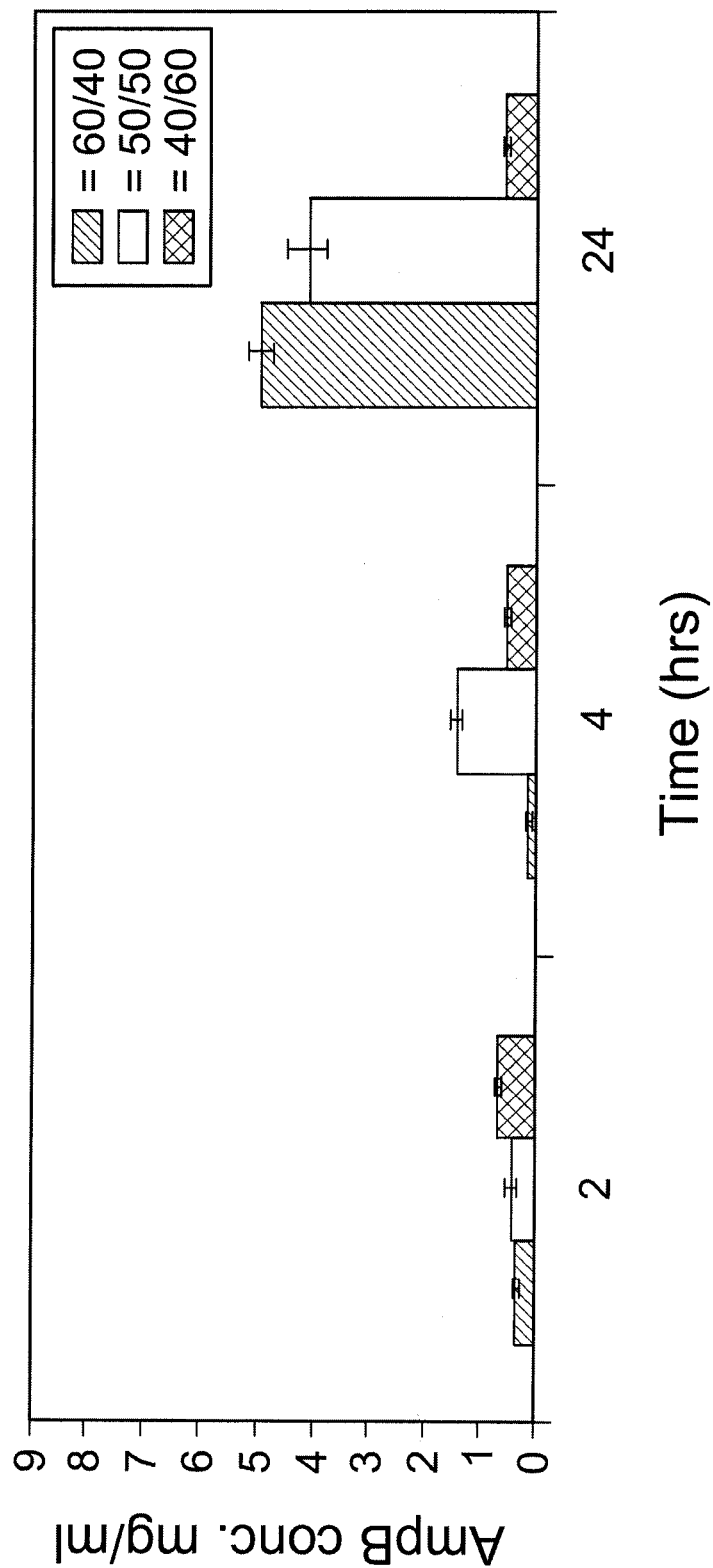
Figure 11:
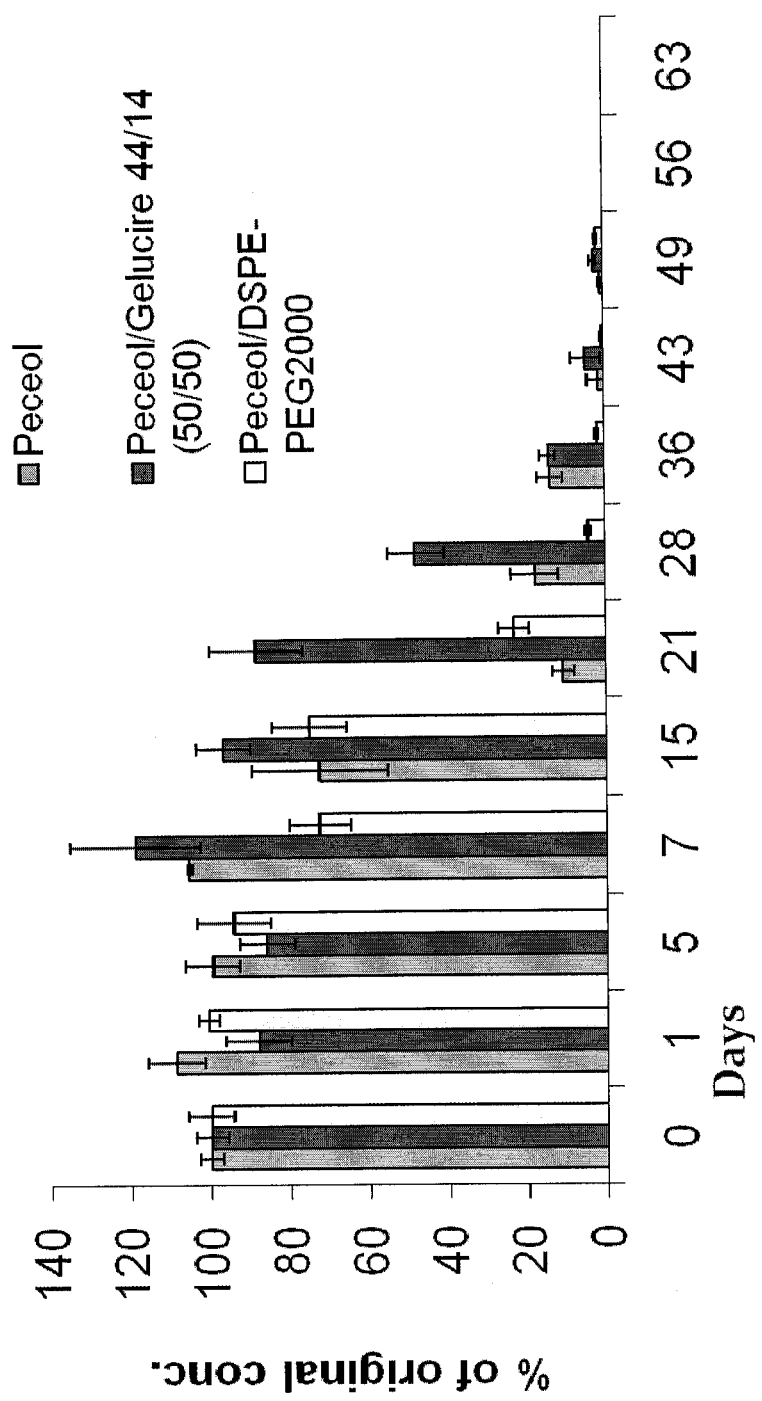
FIG. 11 compares AmpB concentration (% original concentration, 5 mg/mL) over time (0, 1, 5, 7, 15, 21, 28, 36, 43, 49, and 56 days) for an AmpB/PECEOL® formulation (designated PECEOL®) and representative AmpB formulations of the invention (AmpB/PECEOL®GELUCIRE® 44/14, 50/50; and AmpB/PECEOL®/DSPE-PEG-2000, 15 mM DSPE-PEG-2000).

The solubility of representative amphotericin B formulations of that include polyethylene oxide-containing fatty acid esters is illustrated in FIGS. 10A-10C. FIGS. 10A, 10B, and 10C compare AmpB concentration (mg/mL) in representative AmpB formulations of the invention (AmpB/PECEOL®GELUCIRE® 44/14; AmpB/PECEOL®/GELUCIRE® 50/13; and AmpB/PECEOL®/GELUCIRE® 53/10) at varying ratios of PECEOL®:GELUCIRE® (60:40; 50:50; and 40:60 v/v) at 2, 4 and 24 hrs (AmpB measured by UV absorbance of centrifuged samples after specified time at 45° C.). FIG. 11 compares AmpB concentration (% original concentration, 5 mg/mL) over time (0, 1, 5, 7, 15, 21, 28, 36, 43, 49, and 56 days) for an AmpB/PECEOL® formulation (designated PECEOL®) and representative AmpB formulations of the invention (AmpB/PECEOL®/GELUCIRE® 44/14, 50/50; and AmpB/PECEOL®/DSPE-PEG-2000, 15 mM DSPE-PEG-2000) (AmpB measured by UV absorbance of centrifuged samples after specified time at 43° C.). Of the formulations evaluated, the AmpB/PECEOL®/GELUCIRE® 44/14, 50/50, formulation shows the greatest stability, up to 21 days.

To determine their effectiveness as orally administered formulations, the stability of representative amphotericin B formulations of the invention was evaluated in simulated gastric fluid.

Figure 12:
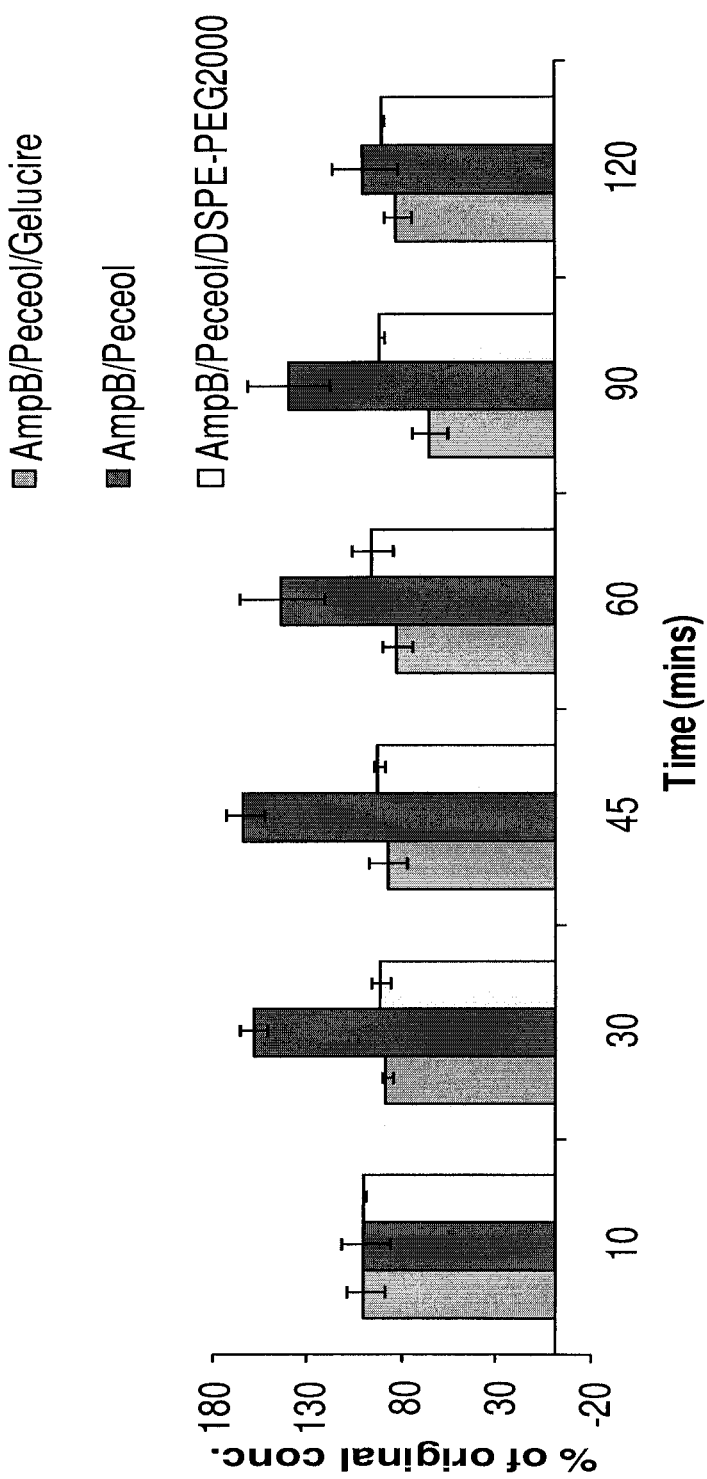
FIG. 12 compares AmpB concentration (% original concentration, 5 mg/mL) over time (10, 30, 45, 60, 90, and 120 min) in simulated gastric fluid (SGF) for an AmpB/PECEOL® formulation and representative AmpB formulations of the invention (AmpB/PECEOL®/GELUCIRE® 44/14, 50/50; and AmpB/PECEOL®/DSPE-PEG-2000, 15 mM DSPE-PEG-2000).

FIG. 12 compares AmpB concentration (% original concentration, 5 mg/mL) over time (10, 30, 45, 60, 90, and 120 min) in simulated gastric fluid (SGF) for an AmpB/PECEOL® formulation and representative AmpB formulations of the invention (AmpB/PECEOL®/GELUCIRE® 44/14, 50/50; and AmpB/PECEOL®/DSPE-PEG-2000, 15 mM DSPE-PEG-2000) (AmpB measured by UV absorbance of centrifuged samples after specified time at 37° C. in SGF, 30 mM NaCl at pH 1.2).

Figure 13:
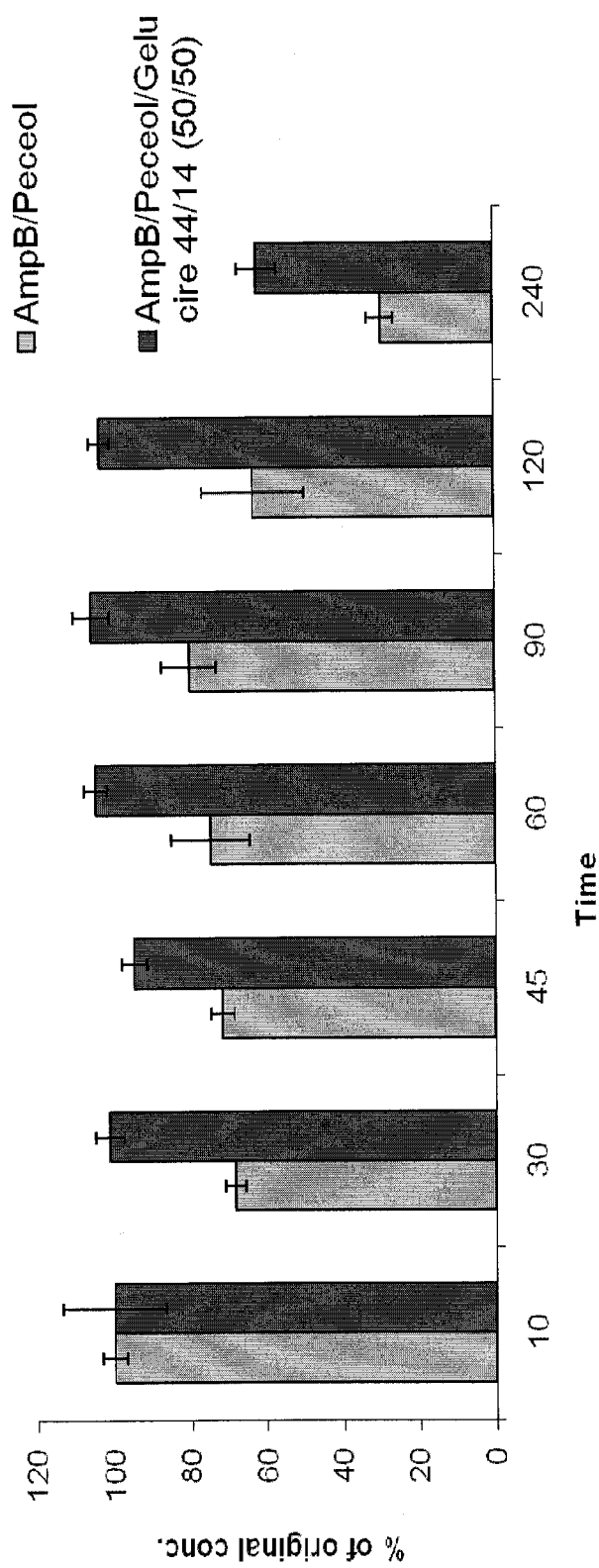
FIG. 13 compares AmpB concentration (% original concentration, 5 mg/mL) over time (10, 30, 45, 60, 90, 120, and 240 min) in fed-state simulated intestinal fluid (FeSSIF) for an AmpB/PECEOL® formulation and a representative AmpB formulation of the invention (AmpB/PECEOL®/GELUCIRE® 44/14, 50/50).

FIG. 13 compares AmpB concentration (% original concentration, 5 mg/mL) over time (10, 30, 45, 60, 90, 120, and 240 min) in fed-state simulated intestinal fluid (FeSSIF) for an AmpB/PECEOL® formulation and a representative AmpB formulation of the invention (AmpB/PECEOL®/GELUCIRE® 44/14, 50/50) (AmpB measured by UV absorbance of centrifuged samples after 4 hrs in FeSSIF, which contains potassium chloride (15.2 g/L), sodium taurolaurate (15 mM), egg phosphatidylcholine (3.75 mM), and acetic acid, adjusted to pH 5.0). The representative formulation of the invention demonstrates consistent AmpB concentration for up to 2 hours.

Figure 14:
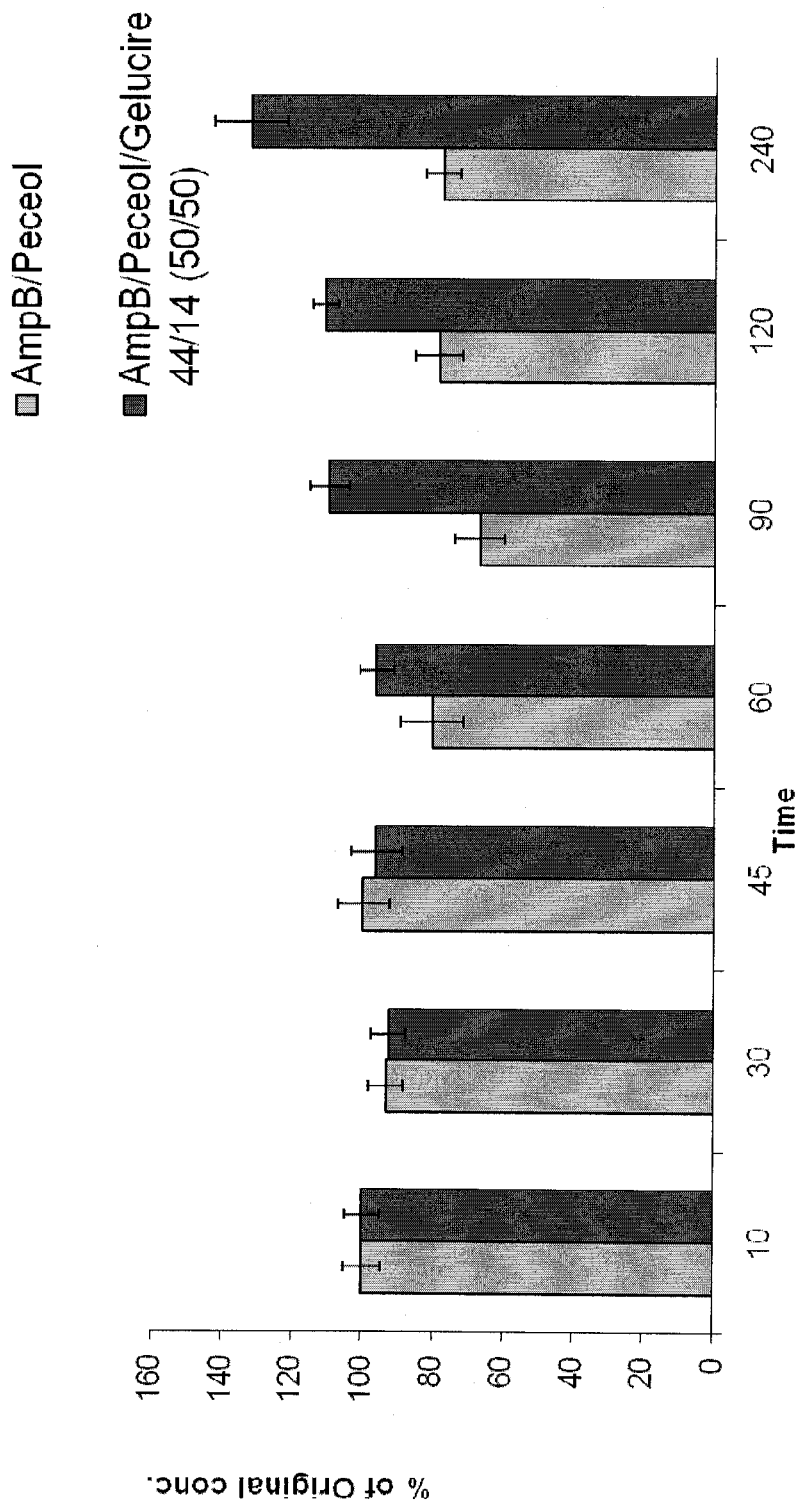
FIG. 14 compares AmpB concentration (% original concentration, 5 mg/mL) over time (10, 30, 45, 60, 90, 120, and 240 min) in fed-state simulated intestinal fluid (FeSSIF) with enzyme for an AmpB/PECEOL® formulation and a representative AmpB formulation of the invention (AmpB/PECEOL®GELUCIRE® 44/14, 50/50).

FIG. 14 compares AmpB concentration (% original concentration, 5 mg/mL) over time (10, 30, 45, 60, 90, 120, and 240 min) in fed-state simulated intestinal fluid (FeSSIF) with enzyme for an AmpB/PECEOL® formulation and a representative AmpB formulation of the invention (AmpB/PECEOL®/GELUCIRE® 44/14, 50/50) (AmpB measured by UV absorbance of centrifuged samples after 4 hrs in FeSSIF, which contains potassium chloride (15.2 g/L), sodium taurolaurate (7.5 mM), egg phosphatidylcholine (2.0 mM), glyceryl monooleate (5.0 mM), sodium oleate (0.8 mM), pancreatin (1000 u lipase/L), and acetic acid, adjusted to pH 5.8). The representative formulation of the invention demonstrates consistent AmpB concentration for up to 2 hours.

Figure 15:
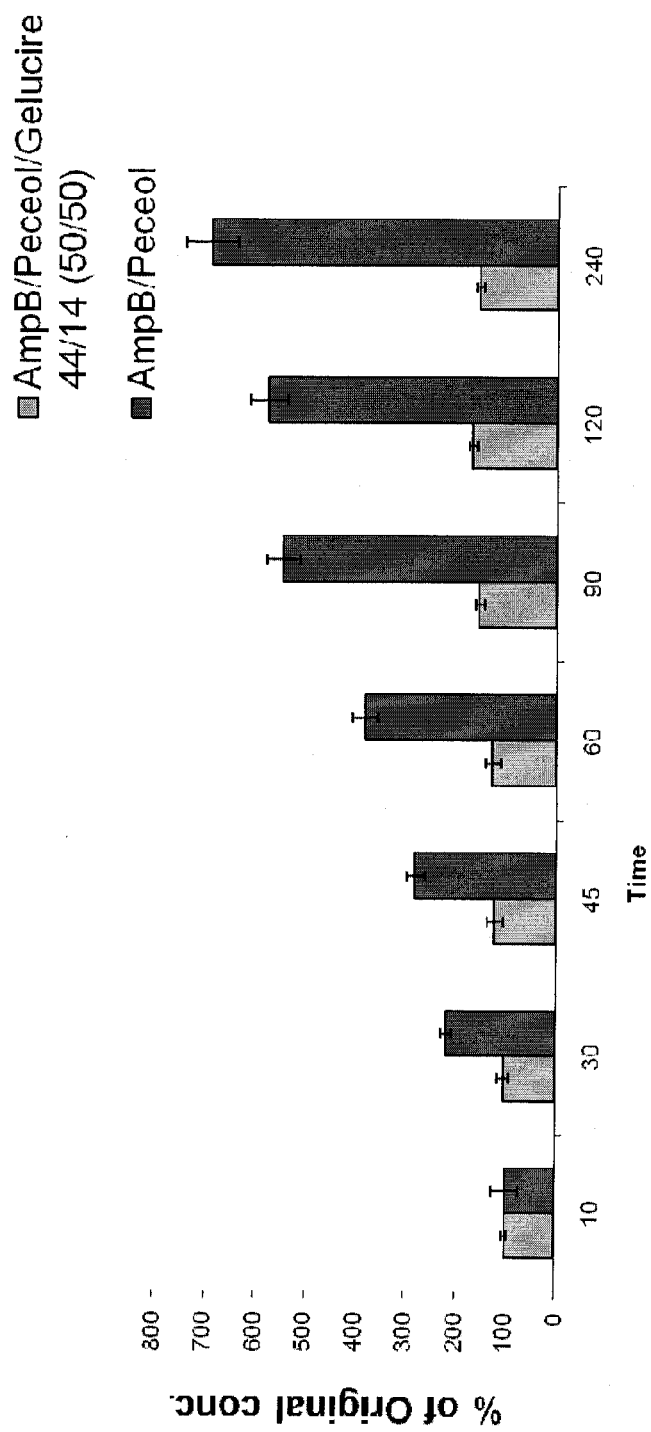
FIG. 15 compares AmpB concentration (% original concentration, 5 mg/mL) over time (10, 30, 45, 60, 90, 120, and 240 min) in fasted-state simulated intestinal fluid (FaSSIF) for an AmpB/PECEOL® formulation and a representative AmpB formulation of the invention (AmpB/PECEOL® GELUCIRE® 44/14, 50/50).
Figure 16:
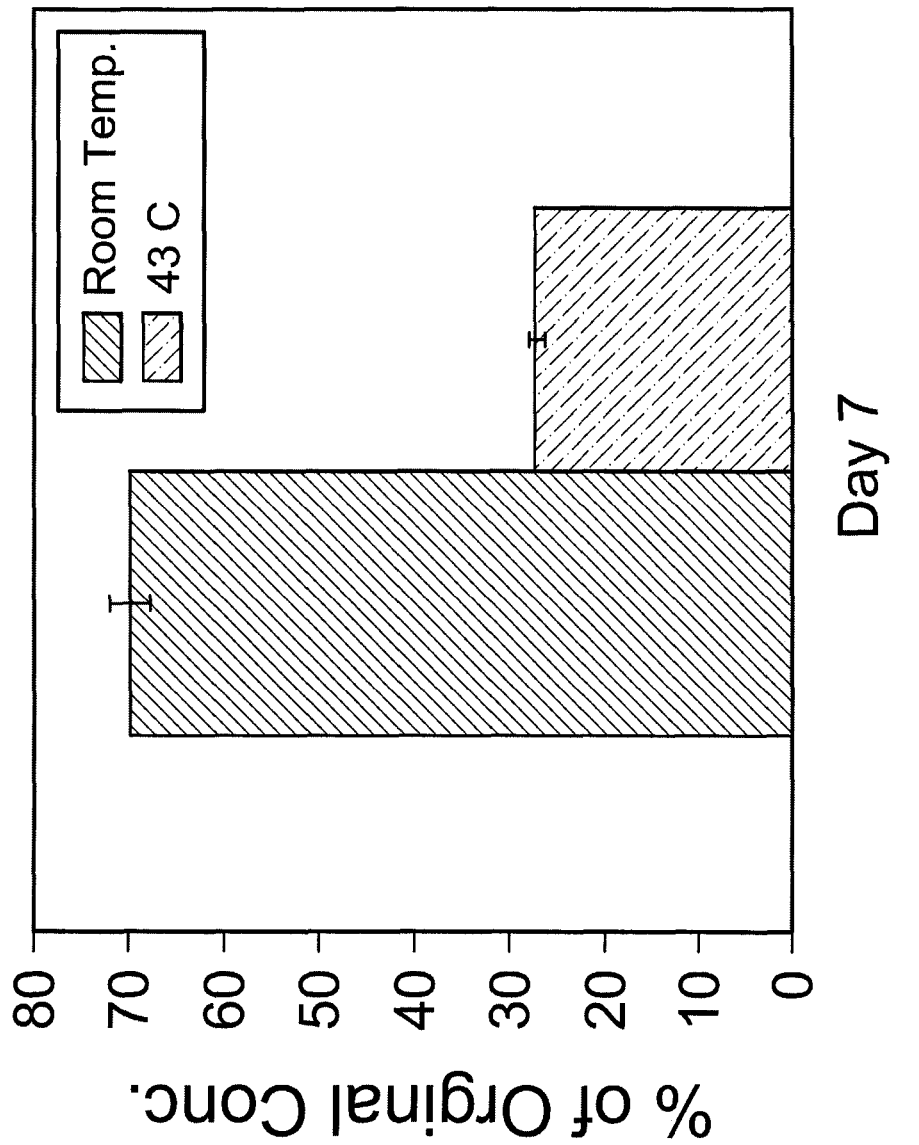
FIG. 16 compares AmpB concentration (% original concentration, 10 mg/mL) of a representative AmpB formulation of the invention (AmpB/PECEOL®/DSPE-PEG-2000, 15 mM DSPE-PEG-2000) after seven days at room temperature and 43° C. (AmpB measured by UV absorbance of centrifuged samples after specified time).

FIG. 15 compares AmpB concentration (% original concentration, 5 mg/mL) over time (10, 30, 45, 60, 90, 120, and 240 min) in fasted-state simulated intestinal fluid (FaSSIF) for an AmpB/PECEOL® formulation and a representative AmpB formulation of the invention (AmpB/PECEOL®/GELUCIRE® 44/14, 50/50) (AmpB measured by UV absorbance of centrifuged samples after 4 hrs in FaSSIF, which contains potassium chloride (7.7 g/L), dibasic potassium phosphate (3.9 g/L), sodium taurolaurate (3.0 mM), egg phosphatidylcholine (0.75 mM), and acetic acid, adjusted to pH 6.5). The representative formulation of the invention demonstrates consistent AmpB concentration for up to 2 hours.

Each of the evaluated representative formulations of the invention demonstrated stability in the simulated fluids over the time period evaluated. The stability of the representative amphotericin B formulations in the GI fluids demonstrates their suitability as orally administered formulations.

Self-Emulsifying Drug Delivery Systems.

The amphotericin B formulations of the invention can be self-emulsifying drug delivery systems. Self-emulsifying drug delivery systems (SEDDS) are isotropic mixtures of oils, surfactants, solvents, and co-solvents/surfactants. SEDDS can be used for the design of formulations in order to improve the oral absorption of highly lipophilic drug compounds, such as amphotericin B. When a SEDDS composition is released into the lumen of the gut, the composition disperses to form a fine emulsion, so that the drug remains in solution in the gut, avoiding the dissolution step that frequently limits the rate of absorption of hydrophobic drugs from the crystalline state. The use of SEDDS usually leads to improved bioavailability and/or a more consistent temporal profile of absorption from the gut. A description of compositions of SEDDS can be found in C. W. Pouton, *Advanced Drug Delivery Reviews* 25: 47-58 (1997).

The amphotericin B formulations of the invention can be orally administered in soft or hard gelatin capsules and form fine relatively stable oil-in-water (o/w) emulsions upon aqueous dilution owing to the gentle agitation of the gastrointestinal fluids. The efficiency of oral absorption of the drug compound from the SEDDS depends on many formulation-related parameters, such as the formulations' components, polarity of the emulsion, droplet size and charge, all of which in essence determine the self-emulsification ability. Thus, only very specific pharmaceutical excipient combinations will lead to efficient self-emulsifying systems.

Methods for Administration and Treatment with Amphotericin B.

The administration of intravenous AmpB has been limited by its dose-dependent kidney toxicity that has not been predictable by monitoring plasma and/or serum drug concentration. A number of studies have reported that AmpB, solubilized in methanol, is poorly absorbed from the gastrointestinal (GI) tract and therefore is not commonly administered orally but intravenously, which can result in the aforementioned renal toxicity. However, to date, few studies investigating the development and assessing the antifungal activity of oral AmpB formulations have been reported.

The effectiveness of representative amphotericin B formulations of the invention that include polyethylene oxide-containing phospholipids in treating fungal infections is described in Example 2. The effectiveness of these formulations for treating *Aspergillus fumigatus* and *Candida albicans* was demonstrated in animal studies.

Treatment of rats infected with *Aspergillus fumigatus* with representative amphotericin B formulations of the invention that include polyethylene oxide-containing phospholipids significantly decreased total fungal CFU concentrations recovered in all the organs added together by 80% compared to non-treated controls (Table 4) without significant changes in plasma creatinine levels (Table 5). ABELCET® treatment significantly decreased total fungal CFU concentrations recovered in all the organs added together by 88% compared to non-treated controls (Table 4) without significant changes in plasma creatinine levels (Table 5).

Figure 7:
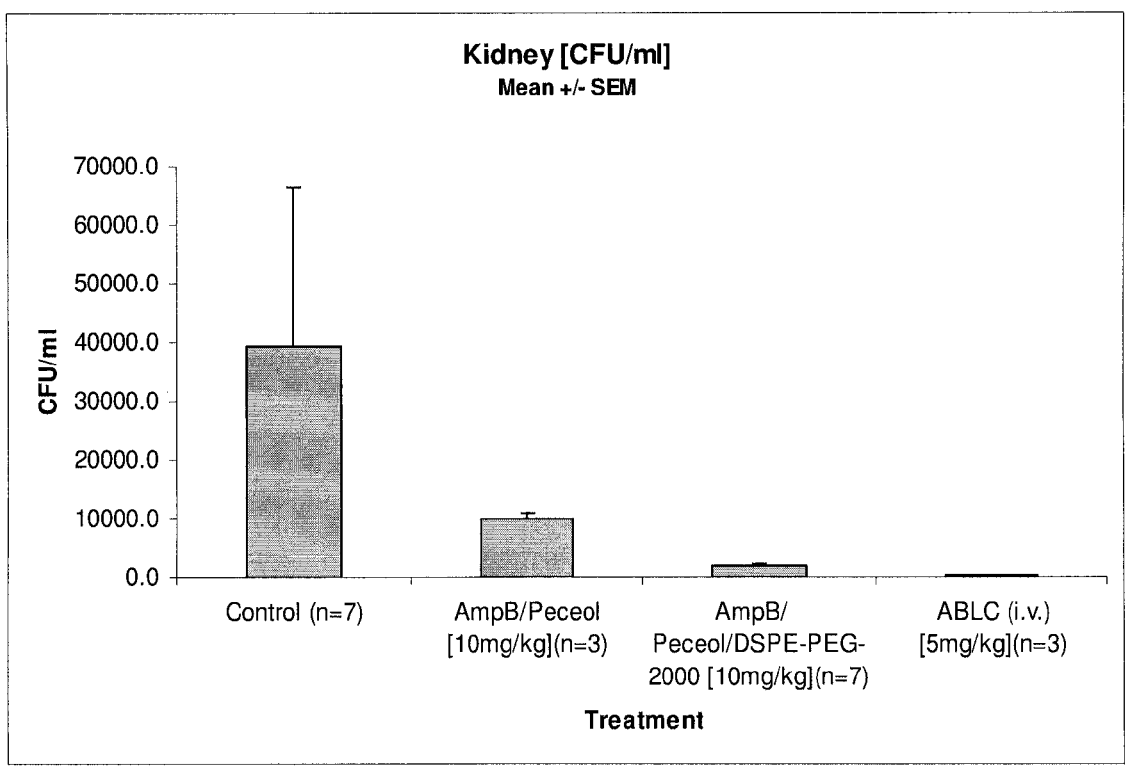
FIG. 7 compares *Candida albicans* concentration (CFU/ml) in the kidneys of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml).
Figure 8:
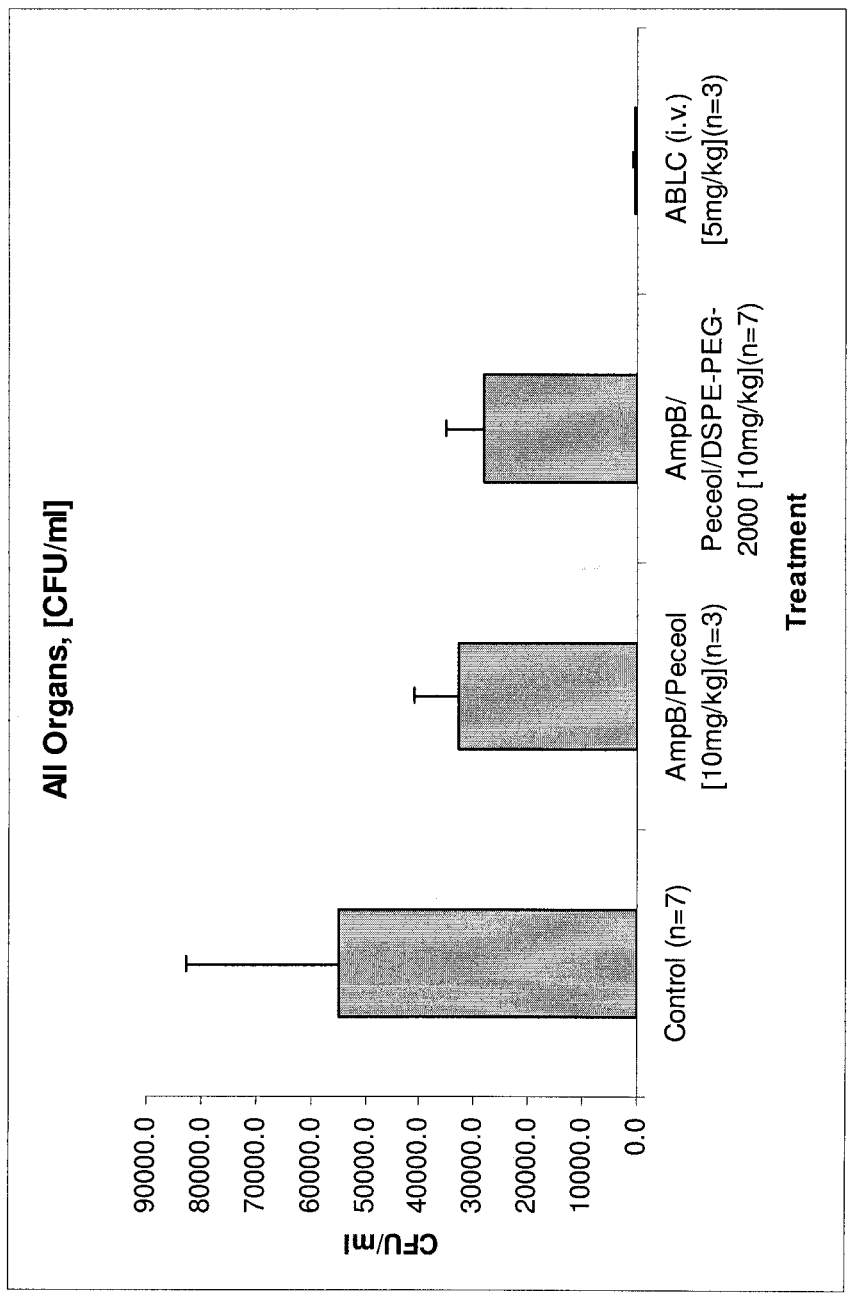
FIG. 8 compares *Candida albicans* concentration (CFU/ml) in the organs of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml).
Figure 9:
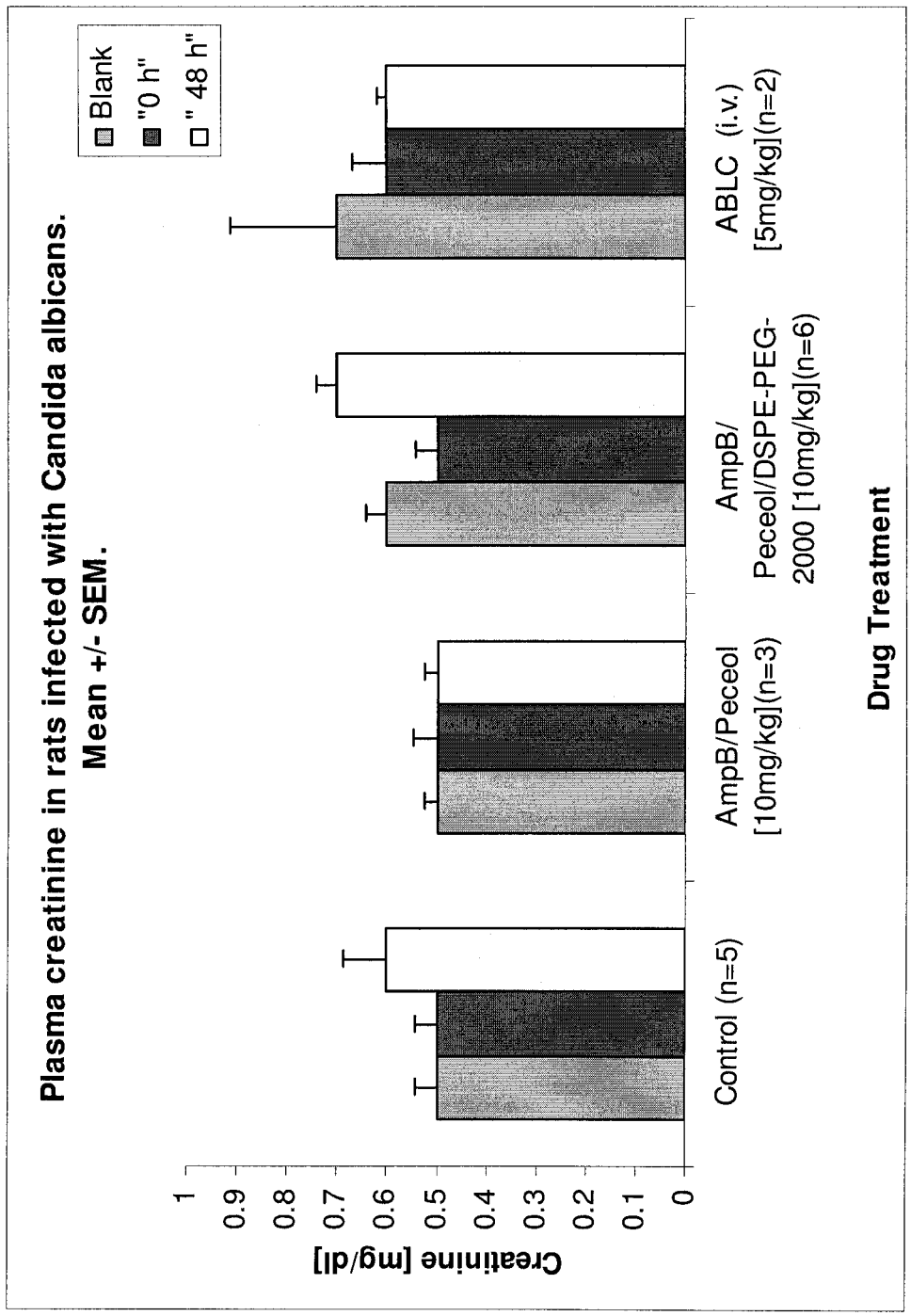
FIG. 9 compares plasma creatinine (mg/dl) in rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml) (blank, 0 hr, and 48 hr).

The results for *Candida albicans* are similar to those for *Aspergillus fumigatus*. Fungal analysis of the kidneys of *Candida albicans*-infected rats treated with a representative AmpB formulation of the invention demonstrate significantly decreased total fungal CFU concentrations compared to control. FIG. 7 compares *Candida albicans* concentration (CFU/ml) in the kidneys of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml). FIG. 8 compares *Candida albicans* concentration (CFU/ml) in the organs of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml). The effectiveness of the representative AmpB formulation in reducing *Candida albicans* concentration was comparable to ABELCET®. Treatment with the representative AmpB formulation significantly decreased total fungal CFU concentrations recovered in the kidneys without significant changes in plasma creatinine levels. FIG. 9 compares plasma creatinine (mg/dl) in rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml) (blank, 0 hr, and 48 hr). No renal toxicity was observed as measured by plasma creatine levels.

In another aspect, the invention provides a method for treating an infectious disease treatable by the administration of amphotericin B. In the method, a therapeutically effective amount of an amphotericin B formulation of the invention is administered to a subject in need thereof. In one embodiment, the formulation is administered orally. In another embodiment, the formulation is administered topically.

As used herein, the terms "treating" and "treatment" refer to reduction in severity and/or frequency of symptoms, elimination of symptoms and/or underlying cause, reduction in likelihood of the occurrence of symptoms and/or underlying cause, and improvement or remediation of damage. Thus, "treating" a patient with an active agent as provided herein includes prevention of a particular condition, disease or disorder in a susceptible individual as well as treatment of a clinically symptomatic individual. As used herein, "effective amount" refers to an amount covering both therapeutically effective amounts and prophylactically effective amounts. As used herein, "therapeutically effective amount" refers to an amount that is effective to achieve the desired therapeutic result. A therapeutically effective amount of a given active agent will typically vary with respect to factors such as the type and severity of the disorder or disease being treated and the age, gender, and weight of the patient.

Infectious diseases treatable by the method and formulations of the invention include fungal infections (aspergillosis, blastomycosis, candidiasis, coccidioidomycosis, crytococcosis, histoplasmosis, mucormycosis, paracoccidioidomycosis, and sporotrichosis), visceral leishmaniasis, cutaneous leishmaniasis, Chagas disease, and Febrile neutropenia. Amphotericin B has been shown to bind to amyloid and prevent the formulation of fibrils. Amphotericin B has been indicated as useful for the treatment of Alzheimer's disease. Accordingly, the amphotericin B formulation of the invention can be used in the treatment of Alzheimer's disease.

In summary, in one aspect, the present invention provides amphotericin B formulations that can be orally administered. The amphotericin B formulations of the invention provide excellent drug solubilization, drug stability in simulated gastric and intestinal fluids, and have significant antifungal activity without the dose-limiting renal toxicity for which the parenteral formulations of amphotericin B are well known.

Therapeutic Agent Formulations

In another aspect, the present invention provides formulations for the delivery of therapeutic agents, methods for making the formulations, and methods for administering the therapeutic agents using the formulations.

In one aspect, the invention provides a formulation for the delivery of a therapeutic agent. The therapeutic agent formulation includes (a) a therapeutic agent;

(b) one or more fatty acid glycerol esters; and (c) one or more polyethoxylated lipids such as one or more polyethylene oxide-containing phospholipids or one or more polyethylene oxide-containing fatty acid esters.

In the therapeutic agent formulation above, the fatty acid glycerol esters, the polyethylene oxide-containing phospholipids, and the polyethylene oxide-containing fatty acid esters are as described above for the amphotericin B formulations. The amounts of these components in the above therapeutic agent formulation is also as described above for the amphotericin B formulations. The therapeutic agent can be present in the formulation in an amount from about 0.1 mg/mL to about 25 mg/mL of the formulation. In certain embodiments, the formulations can further include glycerol in an amount less than about 10% by weight.

The therapeutic drug formulation of the invention advantageously solubilizes difficulty soluble therapeutic drugs. Representative therapeutic agents that can be advantageously formulated and delivered by the formulation and methods of the invention include anticancers, antibiotics, antiviral drugs, antimycotics, anti-prions, anti-amoebics, non-steroidal anti-inflammatory drugs, anti-allergics, immunosuppressive agents, coronary drugs, analgesics, local anesthetics, anxiolytics, sedatives, hypnotics, migraine relieving agents, drugs against motion sickness, and anti-emetics.

Specific therapeutic agents that can be advantageously formulated and delivered by the formulation and methods of the invention include tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfiram, vitamin K, paclitaxel, docetaxel, camptothecin, SN38, cisplatin, and carboplatin.

In certain embodiments, the therapeutic agent formulation of the invention can include a second therapeutic agent.

The therapeutic agent formulation can be a self-emulsifying drug delivery system.

In one embodiment, the therapeutic agent formulation includes
(a) a therapeutic agent;
(b) one or more fatty acid glycerol esters (e.g., oleic acid glycerol esters); and
(c) one or more polyethylene oxide-containing phospholipids (e.g., a distearoylphosphatidyl ethanolamine polyethylene glycol salt).

In one embodiment, the therapeutic agent formulation of the invention includes a therapeutic agent, PECEOL®, and a distearoylphosphatidyl ethanolamine polyethylene glycol salt. In this embodiment, the distearoylphosphatidyl ethanolamine polyethylene glycol salt is present in an amount up to about 30 mM.

In another embodiment, the therapeutic agent formulation includes
(a) a therapeutic agent;
(b) one or more fatty acid glycerol esters (e.g., oleic acid glycerol esters); and
(c) one or more polyethylene oxide-containing fatty acid esters (e.g., lauric, palmitic and/or stearic acid esters of polyethylene glycol).

In one embodiment, the therapeutic agent formulation of the invention includes a therapeutic agent, PECEOL®, and GELUCIRE® 44/14. In another embodiment, the formulation includes a therapeutic agent, PECEOL®, and GELUCIRE® 50/13. In a further embodiment, the formulation includes a therapeutic agent, PECEOL®, and GELUCIRE® 53/10. In these embodiments, the ratio of PECEOL® to GELUCIRE® can be from 20:80 to 80:20 (e.g., 20:80, 30:70; 40:60; 50:50; 60:40; 70:30; and 80:20).

The formulation of two representative therapeutic agents, econazole and docetaxel, is described in Examples 3 and 4, respectively.

In another aspect, the invention provides a method for administering a therapeutic agent. In the method, a therapeutically effective amount of the therapeutic agent is administered using the therapeutic agent formulation described above. In one embodiment, the formulation is administered orally. In another embodiment, the formulation is administered topically.

In further aspects, the invention provides methods for treating conditions and diseases treatable by therapeutic agents formulated in accordance with the present invention. In the methods, an effective amount of a therapeutic drug formulation of the invention is administered to a subject in need thereof. The methods for treating conditions and diseases use formulations of the therapeutic agent families and specific therapeutic agents disclosed herein.

Therapeutic Drug Carrier

In a further aspect, the present invention provides compositions for formulating a therapeutic agent, methods for making the composition, and methods for formulating a therapeutic agent for delivery using the composition.

In one aspect, the invention provides a composition for formulating a therapeutic agent for delivery. The composition includes
(a) one or more fatty acid glycerol esters; and
(b) one or more polyethoxylated lipids such as one or more polyethylene oxide-containing phospholipids or one or more polyethylene oxide-containing fatty acid esters.

In the composition above, the fatty acid glycerol esters, the polyethylene oxide-containing phospholipids, and the polyethylene oxide-containing fatty acid esters are as described above for the amphotericin B formulations. The amounts of these components in the above composition is also as described above for the amphotericin B formulations. In certain embodiments, the compositions can further include glycerol in an amount less than about 10% by weight.

The composition advantageously solubilizes difficulty soluble therapeutic drugs for their delivery. With the incorporation of a therapeutic agent, the composition can be provide a self-emulsifying drug delivery system.

In one embodiment, the composition includes
(a) one or more fatty acid glycerol esters (e.g., oleic acid glycerol esters); and
(b) one or more polyethylene oxide-containing phospholipids (e.g., a distearoylphosphatidyl ethanolamine polyethylene glycol salt).

In one embodiment, the composition includes PECEOL® and a distearoylphosphatidyl ethanolamine polyethylene glycol salt. In this embodiment, the distearoylphosphatidyl ethanolamine polyethylene glycol salt is present in an amount up to about 30 mM.

In another embodiment, the composition includes
(a) one or more fatty acid glycerol esters (e.g., oleic acid glycerol esters); and
(b) one or more polyethylene oxide-containing fatty acid esters (e.g., lauric, palmitic and/or stearic acid esters of polyethylene glycol).

In one embodiment, the composition includes PECEOL® and GELUCIRE® 44/14. In another embodiment, the composition includes PECEOL® and GELUCIRE® 50/13. In a further embodiment, the composition includes PECEOL® and GELUCIRE® 53/10. In these embodiments, the ratio of PECEOL® to GELUCIRE® can be from 20:80 to 80:20 (e.g., 20:80, 30:70; 40:60; 50:50; 60:40; 70:30; and 80:20).

In another aspect, the invention provides a method for making a therapeutic agent formulation. In one embodiment of the method, a therapeutic agent is combined with the composition described above. In another embodiment of the method, a therapeutic agent is combined with one of the components of the composition (e.g., one or more fatty acid glycerol esters) to provide a first combination followed by combining the first combination with the other component of the composition (e.g., one or more polyethylene oxide-containing phospholipids, or one or more polyethylene oxide-containing fatty acid esters).

The formulations and compositions of the invention described herein include (i.e., comprise) the components recited. In certain embodiments, the formulations and compositions of the invention include the recited components and other additional components that do not affect the characteristics of the formulations and compositions (i.e., the formulations and compositions consist essentially of the recited components). Additional components that affect the formulations' and compositions' characteristics include components such as additional therapeutic agents that disadvantageously alter or affect therapeutic profile and efficacy of the formulations or compositions, additional components that disadvantageously alter or affect the ability of the formulations and compositions to solubilize the recited therapeutic agent components, and additional components that disadvantageously alter or affect the ability of the formulations and compositions to increase the bioavailability of the recited therapeutic agent components. In other embodiments, the formulations and compositions of the invention include only (i.e., consist of) the recited components.

The following examples are provide for the purpose of illustrating, not limiting, the invention.

EXAMPLES

Materials

The following materials were used as described in the following examples.

Amphotericin B (from *Streptomyces* sp., Calbiochem, >86% purity) was purchased from EMD Biosciences (San Diego, Calif.) and used without further purification. Amphotericin B as the commercially available deoxycholate micelle dispersion (FUNGIZONE®) was purchased from Vancouver General Hospital pharmacy. Phospholipids and poly(ethylene glycol)-lipids were all from Avanti Polar Lipids (Alabaster, Ala.). HPLC grade solvents were from Fluka. PECEOL® (glyceryl oleate), LABRASOL® (caprylocaproyl macrogol glycerides) and GELUCIRE® 44/14, GELUCIRE® 50/13, and GELUCIRE® 53/10 were obtained from Gattefossé Canada (Mississauga, Ontario). CAPTEX 355® and CAPMUL® were obtained from Abitech. Simulated gastric fluid (SGF) without enzymes was composed of 30 mM NaCl, titrated to pH 1.2 with 1N HCl. Simulated intestinal fluid with pancreatin enzymes (SIFe) was prepared according to the US Pharmacopeia method (USP28) as modified by Vertzoni et al., Dissolution media simulating the intralumenal composition of the small intestine: physiological issues and practical aspects, J. Pharmacy and Pharm. 56(4):453-462 (2004), and was composed of 0.2M NaOH, 6.8 g/L of monobasic potassium phosphate and 10 g/L of pancreatin (Sigma), adjusted to pH 7.5 with NaOH. Fasted-state simulated intestinal fluid with bile salts (FaSSIF) (Vertzoni et al.) was composed of 3 mM sodium taurocholate (Sigma), 3.9 g/L sodium dihydrogen phosphate, 6.2 g/L NaCl in water, either with or without 0.75 mM lecithin and then titrated to pH 6.5 with NaOH. Water was purified by a reverse osmosis system and filtered (0.2 μm) prior to use. All other chemicals were of reagent grade purchased from SigmaAldrich.

Example 1

The Preparation and Characterization of Representative Amphotericin B Formulations In this example the preparation and characterization of representative amphotericin formulations of the invention are described.

Preparation of Self-Emulsifying Drug Delivery Systems (SEDDS).

Amphotericin B (AmpB) was mixed with the SEDDS lipid vehicles by combining the drug powder with the lipids followed by mild heating and stirring (45° C. for 1-2 h), protected from light. Any visible remaining drug particulates were removed by centrifugation at 10,000×g for 15 min.

Preparation of AmpB/PECEOL®/DSPE-PEG Formulations.

AmpB was completely dissolved in a mixture of PECEOL® at 5 mg/mL to which 95% ethanol (1:3 v/v) had been added, as well as 15 mM distearoyl phosphatidylethanolamine (DSPE)-poly(ethylene glycol)$_n$ (PEG) (where n is the average PEG molecular weight, 350, 550, 750 or 2000). AmpB concentration was 3 mg/ml in the ethanol and 5 mg/mL in the PECEOL®, respectively, to allow for complete drug solubilization in the initial mixture. The solution was stirred at 40° C. for 1 h, protected from light, to dissolve AmpB and lipids, followed by solvent evaporation at 40° C. with under vacuum (65 mbar) over several hours in a rotary evaporator. Ethanol was considered to be completely removed by achieving the original weight of the sample containing AmpB, PECEOL®, and lipids measured immediately prior to the addition of the ethanol. A translucent yellow mixture without particulates was formed. No degradation or spectral shape changes of AmpB were observed following this processing.

Characterization of Amphotericin B Stability.

Drug concentrations were measured by reverse-phase HPLC/UV or by UV spectrophotometry ($\lambda$=407 nm). For HPLC analysis of AmpB, samples were diluted in 20% (v/v) methanol in DMSO and 20 μL were injected on a Luna 5 μm (2.0×150 mm) C18 column (Phenomenex) at 30° C. The mobile phase was 10 mM sodium acetate and acetonitrile using a gradient program on a Waters 996 HPLC system, detected by a Waters photodiode array detector ($\lambda$=408 nm). Run time was 13 min and retention time was approximately 8.5 min. Stability of AmpB against decomposition or super-aggregation upon mild heating of the lipid vehicles during drug solubilization and upon storage (21° C.) over 14 days was assessed by UV spectral shift analysis using a Thermoscan UV/visible spectrophotometer with $\lambda$=250-500 nm.

Solubility, Physical Stability, and Self-Emulsification.

SEDDS (self-emulsifying drug delivery systems) formulations had AmpB solubilities ranging from 100-500 μg/mL as measured by HPLC, compared to negligible solubility in aqueous solution (pH 7). For the tested self-emulsifying lipid mixtures, 3 mg of AmpB powder were combined with 0.3 ml (10 mg/mL) of the various lipid combination and the mixture was stirred in a 1 mL amber glass vial at 37° C. for 2 h. Following mixing, the samples were centrifuged at 10,000×g for 15 min to remove any remaining drug particulates. This procedure does not sediment the lipid components. The samples were then dispersed as a 1:1000 (v/v) dilution in 150 mM NaCl with vigorous mixing at 37° C. for 30 min.

The results for CAPTEX® 355-based AmpB SEDDS are summarized in Table 1. The results for PECEOL®/GELUCIRE®-based AmpB SEDDS are summarized in Table 2.

TABLE 1

CAPTEX ® 355-based Amphotericin B Preliminary SEDDS.

| Components (% v/v) | | | | Effective Hydro-dynamic | Subpopulations | |
|---|---|---|---|---|---|---|
| CAPTEX ® 355 | Tween 80 | CAPMUL ® MCM | NaH$_2$PO$_4$ (10 mM, pH 4.0) | Diameter (nm) (Poly-dispersity index) | Diameter range (nm) | Relative pro-portion |
| 50 | 17 | 31 | 2 | 186 (0.232) | 49-69<br>196-277 | 79<br>21 |
| 53 | 5 | 40 | 2 | 237 (0.278) | 24-44<br>111-242<br>614-1334 | 73<br>12<br>15 |
| 58 | 10 | 30 | 2 | 216 (0.258) | 44-64<br>154-255<br>541-893 | 51<br>5<br>44 |
| 63 | 5 | 30 | 2 | 223 (284) | 62-89<br>168-241<br>413-648 | 19<br>6<br>75 |
| 70 | 10 | 18 | 2 | 168 (0.215) | 50-65<br>199-273 | 82<br>18 |
| 50 | 17 | 31 | 2 | 179 (0.24) | 55-71<br>214-297 | 80<br>20 |

Particle sizing was performed after mixture was dispersed 1:1000 (v/v) in 150 mM NaCl at 37° C.×30 min. Relative proportion is based on the cumulative distribution of particle sizes.

TABLE 2

PECEOL ®/GELUCIRE ®-based Amphotericin B SEDDS.

| Components (% v/v) | | Effective Hydrodynamic Diameter (nm) (polydispersity) | Sub-populations (nm) | Relative proportion |
|---|---|---|---|---|
| PECEOL ® | GELUCIRE ® 44/14 | | | |
| 70 | 30 | 156 (0.291) | 20-43<br>75-132<br>307-621 | 55<br>16<br>29 |
| 50 | 50 | 314 (0.319) | 35-62<br>165-332<br>768-1345 | 56<br>5<br>59 |
| 30 | 70 | 252 (0.294) | 28-50<br>135-241<br>568-1160 | 63<br>7<br>30 |
| PECEOL ® | GELUCIRE ® 50/13 | | | |
| 70 | 30 | 158 (0.279) | 30-47<br>94-168<br>336-599 | 55<br>17<br>28 |
| 50 | 50 | 192 (0.301) | 19-22<br>71-145<br>396-704 | 25<br>24<br>51 |
| 30 | 70 | 396 (0.265) | 50-99<br>228-527<br>1703-2382 | 25<br>63<br>12 |

Particle sizing was performed after mixture was dispersed 1:1000 (v/v) in 150 mM NaCl at 37° C.×30 min. Relative proportion is based on the cumulative distribution of particle sizes.

As shown in Tables 1 and 2, the effective hydrodynamic diameter was 168-237 nm at equilibrium for CAPTEX® 355/CAPMUL® MCM/Tween 80 (Table 1) and 58-396 nm for PECEOL®/GELUCIRE® 44/14 (Table 2) but not for formulations based on soybean oil, PECEOL®/LABRASOL®, or PECEOL®/GELUCIRE® 50/13 (>1 μm, data not shown). Importantly, multiple subpopulations of emulsion droplet size were observed. For the CAPTEX® 355-based SEDDS, these subpopulations included diameters consistent with the size of micelles (e.g. 20-50 nm) and all populations remained in the submicron range (Table 1). For the PECEOL®/GELUCIRE® 44/14 mixtures, three subpopulations were observed, including 20-50 nm, 1000-200 nm range (minor population) and those closer to 1 μm in diameter. The proportion of very small and large droplets varied by ratio of components. In the case of PECEOL®/GELUCIRE® 50/13, three subpopulations were also observed with similar droplet size ranges as with PECEOL®/GELUCIRE® 44/14, although there was a trend to slightly larger droplets in the largest diameter subpopulation, which also increased with increasing proportion of GELUCIRE® 50/13 (Table 2). Representative single samples are fully described in the tables, however, it should be noted that replicate samples did show consistency in their effective diameters and in the particle size ranges of the subpopulations. Visual observations were made regarding miscibility, phase separation and precipitation over several days at ambient temperature (21° C.). Several SEDDS formulations remained transparent and homogeneous. For example, the CAPTEX®-based SEDDS formulations all generated semi-transparent mixtures after mixing with 150 mM NaCl that were homogeneous for all combination ratios of CAPTEX®, Tween 80 and sodium phosphate (Table 1). Combinations of PECEOL® and GELUCIRE® 44/14 in the range of 70/30 to 30/70 (v/v) generated a fine emulsion whereas some partial solidification was observed over 24 h at 21° C. when using PECEOL® with GELUCIRE® 50/13, consistent with the high melting point of GELUCIRE® 50/13 (50° C.).

AmpB Solubility in PECEOL®/DSPE-PEG Formulations and Emulsification in Fasted-State Simulated Intestinal Fluid.

The combination of PECEOL® and DSPE-PEG$_n$, where average molecular weight of PEG was varied from 350 to 2000, showed an even greater solubilization of AmpB (5 mg/mL) compared to the preliminary SEDDS formulations. At concentrations ≥10 mg/mL, some precipitation of AmpB did occur upon standing at ambient temperature (21° C.) over 24 h. Upon dispersion in SGF at 37° C. at 0.5 mg/mL followed by stirring for 30 min, the PECEOL®/DSPE-PEG$_{2000}$ AmpB formulations generated translucent emulsions with particle sizes of 300-500 nm and no visible precipitate. In some cases, there appeared to be two populations of submicron particles, with some at 100 nm and others several hundred nm in diameter.

AmpB Stability in Simulated Gastric and Intestinal Fluids.

Amphotericin B in PECEOL®/DSPE-PEG formulations (5 mg/mL) were prepared in triplicate and were incubated in simulated gastric fluid (SGF) as a 1:10 (v/v) dilution or in simulated intestinal fluid prepared with and without lecithin or with enzymes (as described above) as a 1:50 (v/v) dilution at 37° C. with vigorous stirring. Incubation times were 0, 10, 30 or 120 min. At each time point, AmpB concentration was determined by spectrophotometry using triplicate measures of absorbance (407 nm) after complete solubilization in 95% ethanol to clarify the samples, thereby also diluting the samples to the linear range of the UV assay. Values were normalized to the baseline at 330 nm and concentrations were calculated based on an amphotericin B standard curve prepared in each fluid type ($r^2$>0.99). The linearity of the standard curve and concentration range of standards prepared in PECEOL®/DSPE-PEG were not affected by the type of simulated GI fluid or by incubation time, however, separate triplicate standard curves were prepared for each formulation containing the various molecular weights of DSPE-PEG (350, 550, 750, or 2000).

The chemical stability and aggregation state (monomeric vs. self-associated) of AmpB was evaluated in USP simulated gastric fluid as well as fasted-state simulated intestinal fluid with and without bile salts and pancreatin. As described above, AmpB in PECEOL® alone or in PECEOL®/DSPE-PEG formulations (PEG molecular weight=350, 550, 750, or 2000) was prepared at 5 mg/mL and incubated in the simulated GI fluids for a total period of 2 h. At 30 min intervals, the AmpB concentration and UV spectra were evaluated. AmpB exhibits 5 main spectrophotometric peaks in the UV range. Peaks 4 and 5 have the greatest amplitude in monomeric AmpB, whereas there is a left shift when AmpB becomes self-associated. FIG. 3A shows typical UV spectra of AmpB in PECEOL®/DSPE-PEG over the linear range of the UV assay, illustrating the predominance of monomeric AmpB. This pattern was maintained when PEG molecular weight was varied from 350 to 2000 (data not shown). The same spectral pattern was also observed following incubation in SGF, as well as resulting in nearly identical standard curves for the various AmpB/PECEOL®/DSPE-PEG$_n$ preparations, as shown in FIG. 3B.

Regarding chemical stability, the trend was to slightly less drug stability in formulations prepared with DSPE-PEG 350 or 550 compared to DSPE-PEG 750 or 2000. AmpB alone (e.g., neat powder) was not soluble in these media and therefore could not be used properly as a control at comparable concentrations due to the confounding factors of increased dissolution over time vs. degradation. AmpB in PECEOL® alone prepared otherwise the same way was included as a negative control for the stabilizing effect of DSPE-PEG in the formulations. AmpB/PECEOL® showed a trend to slightly less drug stability in SGF than formulations containing DSPE-PEG 350 or 2000 as shown in FIG. 4. FIG. 5 shows AmpB stability in simulated intestinal fluid containing bile salts either without lecithin (FIG. 5A) or with lecithin (FIG. 5B) is less for AmpB in PECEOL® alone or in PECEOL®/DSPE-PEG 350 compared to formulations using the higher PEG molecular weights.

FIG. 6 illustrates the stability of AmpB in simulated intestinal fluid with pancreatin, which contains degradative enzymes. These data suggest better stability of formulations containing DSPE-PEG 750 or 2000 compared to 350 or 550 or in PECEOL® alone. In evaluating the degradation of AmpB in PECEOL® alone, however, is it is important to note that poor mixing of AmpB/PECEOL® in the simulated GI fluids was observed; this formulation tended to float. No changes associated with conversion of the monomeric form vs. aggregated AmpB, such as a difference in the height ratios of specific peaks in the UV spectra or overall pattern, was observed following the full incubation time in the various media described here (data not shown).

Particle Size Analysis.

Particle size analysis by dynamic light scattering (ZetaPALS instrument, Brookhaven Laboratories, New York, operating at 650 nm) was used to assess self-emulsification properties. Emulsion droplet size was measured in physiological saline (150 mM NaCl) following 30 min incubation at 37° C. For PECEOL®/DSPE-PEG AmpB formulations, the mean diameter was measured at 37° C. every 10 min in preliminary experiments and it was found that the mean diameter came to equilibrium by 1 h and remained stable. Drug stability was measured after 2 h, therefore 2 h was the time point used for reported particle size analysis from samples incubated in simulated intestinal fluids. Two data analysis modes are available in the ZetaPALS software (version 3.88), which calculate a weighted mean effective hydrodynamic diameter based on a lognormal distribution, and a multimodal distribution to identify subpopulations centered on two or more mean diameters. Both values are reported where bimodal or multimodal distributions were detected, with the proportion of each subpopulation reported based on the cumulative distribution analysis (ZetaPALS software, version 3.88).

Varying the DSPE-PEG molecular weight had no clear effect on the emulsion droplet size in simulated intestinal fluid (Table 3) following mixing over a period of 2 h at 37° C. Submicron mean diameters were observed in the range of 300-600 nm with a fairly wide polydispersity. A bimodal particle size distribution was also generated, with a small subpopulation centered in submicron range (150-300 nm) and another centered in the 1-2 μm range. AmpB in PECEOL® alone also formed droplets of similar size and distribution in simulated intestinal fluid. These particle size measurements were performed in the absence of lecithin, which formed very large emulsion droplets under the mixing conditions employed and opacified the samples. The results are presented in Table 3.

TABLE 3

PECEOL ®/DSPE-PEG Amphotericin B Formulation Particle Size.

| Formulation: PECEOL ®/ DSPE-PEGnn | Effective Diameter (nm) lognormal distribution | Poly- dispersity index | Sub- populations (nm) | Relative pro- portion |
|---|---|---|---|---|
| 350 | 370 | 0.344 | 129-186 | 20 |
|  |  |  | 888-1282 | 80 |
| 550 | 600 | 0.402 | 108-171 | 20 |
|  |  |  | 1206-1909 | 80 |
| 750 | 596 | 0.395 | 134-210 | 18 |
|  |  |  | 1245-3400 | 82 |
| 2000 | 533 | 0.392 | 119-200 | 30 |
|  |  |  | 1390-2330 | 70 |
| AmpB in PECEOL ® alone | 351 | 0.333 | 128-194 | 20 |
|  |  |  | 738-1120 | 80 |

Particle sizing by dynamic light scattering of AmpB in PECEOL®/DSPE-PEG, where the molecular weight of PEG was varied from 350 to 2000, following 2 h incubation simulated fasted-state intestinal fluid (pH 6.8) at 0.5 mg AmpB/mL. Relative proportion is based on the cumulative distribution of particle sizes.

Example 2

The Effectiveness of Representative Amphotericin B Formulations in Treating Fungal Infections: *Aspergillus Fumigatus* and *Candida Albicans*

In this example, the effectiveness of representative amphotericin B formulations of the invention in treating fungal infections is described. Animal studies were conducted to determine the effectiveness of representative amphotericin B formulations of the invention in treating rats infected with *Aspergillus fumigatus* or *Candida albicans*.

1. *Aspergillus fumigatus* ($2.7$-$3.3 \times 10^7$ colony forming units [CFU]) was injected via the jugular vein; 48 h later male albino Sprague-Dawley rats (350-400 g) were administered either as a single oral gavage of monoglyceride-DSPE/PEG2000-based AmpB (10 mg AmpB/kg; n=7) twice daily for 2 consecutive days, a single intravenous (i.v.) dose of ABELCET® (5 mg AmpB/kg; n=4), or physiologic saline (non-treated controls; n=9) once daily for 2 consecutive days. Organs were harvested at sacrifice (day 3) and processed (see below). Blood was drawn before inoculation (Blank), pre-dose (0 hour) and 48 hours after treatment for plasma creatinine analysis. Male albino Sprague-Dawley rats (350 to 400 g) were purchased from Charles River Laboratories (Wilmington, Mass.). The rats were surgically implanted with a port (Access Technologies) and catheter with access to venous blood by a similar method used for rabbits. The rats were housed in an animal care facility with a 12 hour light-dark cycle and controlled temperature and humidity. The rats were given ad libitum access water and standard rat chow (Purina Rat Chow) for the duration of the study. The ports were primed daily with normal saline and heparin to prevent blockages. The animals were cared for according to principals promulgated by the Canadian Council on Animal Care and the University of British Columbia.

*Aspergillus fumigatus* Inoculum.

*A. fumigatus* were collected from a pool of patients with either disseminated aspergillosis (BC Centre for Disease Control). Cultures were grown on Sabouraud dextrose agar for 48 hours at 37° C. Conidia were isolated by washing the agar with pyrogen free saline. The conidia were suspended by vortexing with glass beads and diluted with pyrogen free saline to obtain between 2.7 to $3.3 \times 10^7$ conidia in 300 ml of saline. Conidia were counted using a hemocytometer and a 100 μl aliquot was serially diluted and aliquots were plated on sabouraud dextrose agar for 48 hours at 37° C. to determine the number of viable conidia and purity of the inoculum. The average percentage of viable conidia in the inoculum was 62%±19. None of the spore suspensions were contaminated with any other organism. Rats were inoculated with 300 μl through the indwelling port 48 hours before the beginning of treatment to allow for aspergillosis to develop.

2. *Candida albicans* ($1$-$1.35 \times 10^6$ colony forming units [CFU]) was injected via the jugular vein; 48 h later male albino Sprague-Dawley rats (350-400 g) were administered either as a single oral gavage of monoglyceride-DSPE/PEG2000-based AmpB (10 mg AmpB/kg; n=7) twice daily for 2 consecutive days, a single intravenous (i.v.) dose of ABELCET® (5 mg AmpB/kg; n=3), or physiologic saline (non-treated controls; n=9) once daily for 2 consecutive days. Organs were harvested at sacrifice (day 3) and processed (see below). Blood was drawn before inoculation (Blank), pre-dose (0 hour) and 48 hours after treatment for plasma creatinine analysis. Male albino Sprague-Dawley rats (350 to 400 g) were purchased from Charles River Laboratories (Wilmington, Mass.). The rats were surgically implanted with a port (Access Technologies) and catheter with access to venous blood by a similar method used for rabbits. The rats were housed in an animal care facility with a 12 hour light-dark cycle and controlled temperature and humidity. The rats were given ad libitum access water and standard rat chow (Purina Rat Chow) for the duration of the study. The ports were primed daily with normal saline and heparin to prevent blockages. The animals were cared for according to principals promulgated by the Canadian Council on Animal Care and the University of British Columbia.

*Candida albicans* Inoculum.

*Candida albicans* were collected from a pool of patients with either disseminated Candidiasis (BC Centre for Disease Control). Cultures were grown on Sabouraud dextrose agar for 48 hours at 37° C. Conidia were isolated by washing the agar with pyrogen free saline. The conidia were suspended by vortexing with glass beads and diluted with pyrogen free saline to obtain between 2.7 to $3.3 \times 10^7$ conidia in 300 μl of saline. Conidia were counted using a hemocytometer and a 100 μl aliquot was serially diluted and aliquots were plated on sabouraud dextrose agar for 48 hours at 37° C. to determine the number of viable conidia and purity of the inoculum. The average percentage of viable conidia in the inoculum was 62%±19. None of the spore suspensions were contaminated with any other organism. Rats were inoculated with 300 μl through the indwelling port 48 hours before the beginning of treatment to allow for aspergillosis to develop.

3. Animal Methods.

One-ml whole blood samples were drawn into pediatric collection tubes (3.6 mg $K_2$ EDTA) before infection (blank), pre-dose (0 hour) and 48 hours after treatment (48 hour). All whole blood samples were mixed by inversion and plasma was separated by centrifugation (15 minutes, 3000 RPM at 4° C.). Plasma samples were stored at −20° C. for creatinine analysis. After the collection of the 48 hour blood specimen, the rat was euthanized with intravenous overdose (1 ml) of EUTHANYL®, (sodium pentobarbital 240 mg/ml). Spleen, right kidney, liver, lung, heart and brain tissue samples were harvested, weighed and placed in sterile containers. Normal saline was added, 1 ml/g of specimen and homogenized (Heidolph diax 900). An aliquot of organ homogenate was stored at room temperature until plating and the remaining sample was placed at −80° C. until HPLC analysis.

The choice of organ colony forming units (CFU) as an indicator of antifungal activity was based on previously published work (K. M. Wasan et al., Assessing the antifungal activity and toxicity profile of Amphotericin B Lipid Complex (ABLC; ABELCET®) in combination with Caspofungin in experimental systemic aspergillosis, Journal of Pharm. Sci. 2004; 93(6):1382-1389). Aliquots of 100 μl full strength organ homogenate and 1:10 dilution (with sterile saline) were each spread plated onto Saboraud Dextrose Agar plates in duplicate. After 48 hr incubation at 37° C., the resulting colonies of *A. fumigatus* or *C. albicans* were counted and averaged over the duplicate plates. The limit of detection of the assay was $0.1 \times 10^2$ CFU/ml homogenate.

Renal toxicity was indirectly assessed, as previously described (K. M. Wasan et al., Assessing the antifungal activity and toxicity profile of Amphotericin B Lipid Complex (ABLC; ABELCET®) in combination with Caspofungin in experimental systemic aspergillosis, Journal of Pharm. Sci. 2004; 93(6):1382-1389), by determining creatinine concentration in plasma using a commercially available kit (Sigma Chemicals Co.). A baseline was determined by measuring creatinine concentration in the blank sample, and was compared to plasma creatinine concentration in the 0 hour (pre-dose), 48 hour samples. For the purposes of this study, a 50% or greater increase in plasma creatinine concentration as compared to baseline was considered to be a sign of renal toxicity.

4. Statistical Analysis.

The number of CFU's in organs and plasma creatinine concentrations prior to and following administration of treatment were compared between each treatment group by analysis of variance (INSTAT2; GraphPad Inc.). Critical differences were assessed by Tukey post hoc tests. Serum creatinine values were compared prior to 48 hours following treatment using repeat measures ANOVA with a Tukey post hoc test to determine critical differences (Prism 4; Graphpad Inc.). A difference was considered significant if the probability of chance explaining the results was reduced to less than 5% ($p<0.05$). All data were expressed as a mean±standard error of the mean.

Antifungal Activity and Renal Toxicity in Rats Infected with *Aspergillus fumigatus*.

PECEOL®/DSPE/PEG2000-based oral AmpB treatment significantly decreased total fungal CFU concentrations recovered in all the organs added together by 80% compared to non-treated controls (Table 4) without significant changes in plasma creatinine levels (Table 5). ABELCET® treatment significantly decreased total fungal CFU concentrations recovered in all the organs added together by 88% compared to non-treated controls (Table 4) without significant changes in plasma creatinine levels (Table 5).

TABLE 4

Fungal analysis of *Aspergillus fumigatus*-infected male Sprague Dawley rats treated with oral gavage doses of Normal Saline (non-treated control), Amphotericin-DSPE-PEG200 incorporated into PECEOL ® (10 mg/kg twice daily × 2 days) or a single intravenous dose of ABELCET ® (ABLC; 5 mg/kg once daily × 2 days).

| Treatment Groups | Infected Tissues (CFU/ml of homogenized tissues) | | | | | | |
|---|---|---|---|---|---|---|---|
| | Brain | Lungs | Heart | Liver | Spleen | Kidney | All Organs |
| Non-treated Controls (n = 9) | 3538 ± 1810 | 74 ± 30 | 101 ± 63 | 308 ± 114 | 1163 ± 772 | 364 ± 119 | 5549 ± 2498 |
| ABLC 5 (n = 4) | 550 ± 445$^a$ | 10 ± 4$^a$ | 15 ± 3$^a$ | 18 ± 5$^a$ | 88 ± 44$^a$ | 10 ± 0$^a$ | 690 ± 419$^a$ |
| AmpB-DSPE-PEG-2000 (n = 7) | 736 ± 186$^a$ | 51 ± 18 | 20 ± 4 | 180 ± 48 | 107 ± 32$^a$ | 44 ± 10$^a$ | 1139 ± 221$^a$ |

All rats were infected with 2.9-3.45 × 10$^7$ Viable Colony Forming Units (CFU)/0.3 ml/rat of *Aspergillus fumigatus* prior to initiation of treatment.
$^a$p < 0.05 vs. non-treated controls using student T-Test; All Data are presented as mean ± SEM.
*Note:
Previous studies have shown that AmpB alone does not have measurable accumulation at the doses used herein. ABLC: Amphotericin B Lipid Complex.

TABLE 5

Plasma creatinine concentrations before infection (blank), pre-dose (0 hour) and 48 hours after treatment (48 hour).

| | Blank | 0 | 48 |
|---|---|---|---|
| Creatinine (mg/dl) Control (n = 9) | 0.4 ± 0.1 | 0.5 ± 0.1 | 0.9 ± 0.2 |

TABLE 5-continued

Plasma creatinine concentrations before infection (blank), pre-dose (0 hour) and 48 hours after treatment (48 hour).

| | Blank | 0 | 48 |
|---|---|---|---|
| AmpB/DSPE-PEG2000/PECEOL ® 10 mg/kg (oral) (n = 7) | 0.6 ± 0.2 | 0.6 ± 0.2 | 0.5 ± 0.1 |
| ABLC 5 mg/kg-IV (n = 4) | 0.3 ± 0.2 | 0.4 ± 0.1 | 0.5 ± 0.1 |

Data Presented as Mean±SEM

The results for *Candida albicans* are similar to those for *Aspergillus fumigatus*. Fungal analysis of the kidneys of *Candida albicans*-infected rats treated with a representative AmpB formulation of the invention demonstrate significantly decreased total fungal CFU concentrations compared to control. FIG. 7 compares *Candida albicans* concentration (CFU/ml) in the kidneys of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml). FIG. 8 compares *Candida albicans* concentration (CFU/ml) in the organs of rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml). The effectiveness of the representative AmpB formulation in reducing *Candida albicans* concentration was comparable to ABELCET®. Treatment with the representative AmpB formulation significantly decreased total fungal CFU concentrations recovered in the kidneys without significant changes in plasma creatinine levels.

FIG. 9 compares plasma creatinine (mg/dl) in rats infected with *Candida albicans* and treated with control, an AmpB/PECEOL® formulation (10 mg/kg), a representative AmpB formulation of the invention (AmpB/PECEOL®/DSPE-PEG-2000, designated AmpB/DSPE-PEG-2000, 10 mg/kg), and intravenous ABELCET® (designated ABLC, 5 mg/ml)

(blank, 0 hr, and 48 hr). No renal toxicity was observed as measured by plasma creatine levels.

Example 3

Representative Econazole Formulation

In this example, the preparation and characterization of a representative econazole formulation of the invention is described. The solubility of econazole in water is <1 mg/mL (19-66° F.), and the solubility in ethanol is ≤20 mg/mL.

Econazole nitrate formulations (10 and 15 mg econazole nitrate/mL formulation) were prepared by a method similar to the method for preparing the amphotericin B formulation described in Example 1. To econazole nitrate (Sigma) and DSPE-PEG2000 (15 mM) powders was added 45° C. PECEOL® and the resulting mixture shaken for 2-4 h at 45° C. in a shaking incubator. No ethanol was used. Samples were centrifuged in order to visualize unsolubilized material. The mixture was then evaluated for clarity over time.

The product econazole nitrate formulation was incubated at 37° C. for 2 h in simulated gastric fluid (1:100 v/v dilution), fasted-state simulated intestinal fluid, and fed-state simulated intestinal fluid with and without pancreatin (all at 1:500 v/v dilution) to evaluate emulsification properties. Emulsion droplet size was evaluated immediately by dynamic light scattering (Zetasizer, Malvern Instruments).

The formulations were evaluated for clarity over time. The results are summarized in Table 6.

TABLE 6

Visual appearance of econazole formulations.

| Econazole Formulation | Visual Appearance | | | |
|---|---|---|---|---|
| | Day 0 | 24 h | 4 days | 5 days |
| 10 mg/mL | Clear | Clear | Clear | Clear > 5 days |
| 15 mg/mL | Some solids remaining after centrifugation | Still clear portion with solids | Not tested | Not tested |

Emulsion droplet size analysis was determined for the econazole formulation (10 mg/mL) in simulated gastric and intestinal fluids (SGF, FaSSIF, FeSSIF, and FeSSIFe), with mean based on peak analysis by volume. Emulsion droplet size in the table refers to the mean and peak half-width, a range for each subpopulation. The results are summarized in Table 8.

TABLE 7

Emulsion droplet size for econazole formulation.

| Media | Dilution factor | Lower size (nm) | Upper size (nm) | Mean (nm) |
|---|---|---|---|---|
| SGF | 100 | 30 | 291 | 72 ± 46 (71%) and 310 ± 200 (29%) |
| FaSSIF | 500 | 59 | 333 | 123 ± 65 (44%) and 342 ± 138 (56%) |
| FeSSIF | 500 | 66 | 1557 | 386 ± 182 (10%); 726 ± 143 (5%) and 2503 ± 565 (85%) |
| FeSSIFe | 500 | 510 | >5000 | 650 ± 150 (75%) >5 μm (25%) |

SGF: simulated gastric fluid
FaSSIF: fasted-state simulated intestinal fluid
FeSSIF: fed-state simulated intestinal fluid
FeSSIFe: fed-state simulated intestinal fluid with pancreatic enzymes (Sigma)

Composition of simulated gastric/intestinal fluids (1 L) used in emulsification studies for the econazole formulation.

SGF (simulated gastric fluid):
Distilled water: 1 L
Sodium chloride: 30 mM (1740 mg/L)
Hydrochloric acid: as required to adjust to pH 1.2.

FaSSIF (fasted-state simulated intestinal fluid):
Dibasic potassium phosphate: 3.9 g
Distilled water: 1 L
Sodium taurocholate: 3 mM (1613.04 mg/L)
Egg phosphatidylcholine: 0.75 mM (570.07 mg/L)
Potassium chloride: 7.7 g
Hydrochloric acid: as required to adjust pH to 6.5.

FeSSIF (fed-state simulated intestinal fluid):
Distilled water: 1 L
Acetic acid: 8.65 g=9.073 ml
Sodium taurocholate: 15 mM (8065.2 mg/L)
Egg phosphatidylcholine: 3.75 mM (2850.34 mg/L)
Potassium chloride: 15.2 g
Hydrochloric acid or sodium hydroxide: as required to adjust pH to 5.0.

FeSSIF with pancreatic enzymes:
Distilled water: 1 L
Sodium taurocholate: 7.5 mM (4032.6 mg/L)
Egg phosphatidylcholine: 2.0 mM (1520.18 mg/L)
Glyceryl monooleate: 5.0 mM (1782.72 mg/L)
Sodium oleate: 0.8 mM (241.96 mg/L)
Pancreatin: 1000 u lipase
Acetic acid: 9.073 ml
Potassium chloride: 15.2 g
Hydrochloric acid or sodium hydroxide: as required to adjust pH to 5.8.

Example 4

Representative Docetaxel Formulation

In this example, the preparation of a representative docetaxel formulation of the invention is described. The solubility of docetaxel in water is about 10-25 μg/mL.

A docetaxel formulation (10 mg docetaxel/mL formulation) was prepared by combining docetaxel (Fluka) powder with the DSPE-PEG2000 powder and wetting the combined powders 100% ethanol to 10% v/v of the final intended volume. The ethanol did not solubilize the powders. To the wetted powders was added PECEOL® that was pre-warmed to 50° C., followed by vortex mixing for 2 min which resulted in a clear solution. Ethanol was not removed.

Ethanol was used with docetaxel as a co-solvent in this formulation to maximize solubility. Docetaxel is poorly water soluble but has polar regions.

The formulation was evaluated for clarity over time. The results are summarized in Table 8.

TABLE 8

Visual appearance of docetaxel formulations.

| Docetaxel Formulation | Visual Appearance | | | |
|---|---|---|---|---|
| | Day 0 | 24 h | 4 days | 5 days |
| 10 mg/mL at 4° C. | — | Solidified at 4° C. but clear upon melting briefly | Solidified at 4° C. but clear upon melting briefly | Solidified at 4° C. but clear upon melting briefly |
| 10 mg/mL at 21° C. | Clear | Clear | Clear | Clear |
| 10 mg/mL at −20° C. | — | Solidified at −20° C. but clear upon melting briefly | Solidified at −20° C. but clear upon melting briefly | Solidified at −20° C. but clear upon melting briefly |
| 10 mg/ml at 50° C. | — | Clear | Clear with yellow tinged* | Clear with yellow tinge* |

*Consistent with color change observed with PECEOL ® alone at 50° C. for this length of time.

Docetaxel formulations of the invention include those as described above, but that do not include ethanol.

While illustrative embodiments have been illustrated and described, it will be appreciated that various changes can be made therein without departing from the spirit and scope of the invention.

The embodiments of the invention in which an exclusive property or privilege is claimed are defined as follows:

1. An amphotericin B formulation, comprising,
   (a) amphotericin B;
   (b) one or more fatty acid glycerol esters; and
   (c) one or more polyethylene oxide-containing fatty acid esters.

2. The formulation of claim 1, wherein amphotericin B is present in the formulation in an amount from about 0.5 to about 10 mg/mL of the formulation.

3. The formulation of claim 1, wherein the fatty acid glycerol esters comprise from about 32 to about 52% by weight fatty acid monoglycerides.

4. The formulation of claim 1, wherein the fatty acid glycerol esters comprise from about 30 to about 50% by weight fatty acid diglycerides.

5. The formulation of claim 1, wherein the fatty acid glycerol esters comprise from about 5 to about 20% by weight fatty acid triglycerides.

6. The formulation of claim 1, wherein the polyethylene oxide-containing fatty acid esters comprise a polyethylene oxide ester of a C8-C22 saturated fatty acid.

7. The formulation of claim 1, wherein the polyethylene oxide-containing fatty acid esters comprise a polyethylene oxide ester of a C12-C18 saturated fatty acid.

8. The formulation of claim 1, wherein the polyethylene oxide-containing fatty acid esters is selected from the group consisting of lauric acid esters, palmitic acid esters, stearic acid esters, and mixtures thereof.

9. The formulation of claim 1, wherein the polyethylene oxide-containing fatty acid esters comprise a polyethylene oxide having an average molecular weight of from about 750 to about 2000.

10. The formulation of claim 1, wherein the ratio of the fatty acid glycerol esters to polyethylene oxide-containing fatty acid esters is from about 20:80 to about 80:20 v/v.

11. The formulation of claim 1, wherein the ratio of the fatty acid glycerol esters to polyethylene oxide-containing fatty acid esters is about 60:40 v/v.

12. The formulation of claim 1, wherein the formulation is a self-emulsifying drug delivery system.

13. A method for treating an infectious disease treatable by the administration of amphotericin B, comprising administering to a subject in need thereof a therapeutically effective amount of an amphotericin B formulation of claim 1.

14. The method of claim 13, wherein the formulation is administered orally or topically.

15. The method of claim 14, wherein the infectious disease is a fungal infection, visceral leishmaniasis, cutaneous leishmaniasis, Chagas disease, or Febrile neutropenia.

16. The method of claim 15, wherein the fungal infection is aspergillosis, blastomycosis, candidiasis, coccidioidomycosis, crytococcosis, histoplasmosis, mucormycosis, paracoccidioidomycosis, or sporotrichosis.

17. The formulation of claim 1, wherein the ratio of the fatty acid glycerol esters to polyethylene oxide-containing fatty acid esters is about 50:50 v/v.

\* \* \* \* \*

UNITED STATES PATENT AND TRADEMARK OFFICE
CERTIFICATE OF CORRECTION

PATENT NO. : 8,592,382 B2
APPLICATION NO. : 12/601676
DATED : November 26, 2013
INVENTOR(S) : Wasan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this
Twenty-sixth Day of May, 2015

Michelle K. Lee
*Director of the United States Patent and Trademark Office*